(12) United States Patent
Laugharn, Jr. et al.

(10) Patent No.: US 7,328,628 B2
(45) Date of Patent: Feb. 12, 2008

(54) APPARATUS AND METHODS FOR SAMPLE PREPARATION

(75) Inventors: James A. Laugharn, Jr., Winchester, MA (US); Brevard S. Garrison, Reading, MA (US)

(73) Assignee: Covaris, Inc., Woburn, MA (US)

( * ) Notice: Subject to any disclaimer, the term of this patent is extended or adjusted under 35 U.S.C. 154(b) by 138 days.

(21) Appl. No.: 11/001,988

(22) Filed: Dec. 2, 2004

(65) Prior Publication Data

US 2005/0132775 A1    Jun. 23, 2005

Related U.S. Application Data

(60) Provisional application No. 60/528,069, filed on Dec. 8, 2003.

(51) Int. Cl.
*G01N 1/38* (2006.01)
*C12M 1/33* (2006.01)
*B01L 3/00* (2006.01)
*B02C 19/18* (2006.01)

(52) U.S. Cl. .................. 73/863; 73/864.91; 241/101.2

(58) Field of Classification Search ..............................
241/101.01–101.2, 101.5, 101.6, 101.8;
73/863, 864.91, 12.01
See application file for complete search history.

(56) References Cited

U.S. PATENT DOCUMENTS 3,604,270 A * 9/1971 Falk ........................ 73/864.59

3,919,558 A * 11/1975 Brouillette et al. ...... 250/443.1
2003/0165482 A1    9/2003 Rolland et al. .......... 424/93.21

FOREIGN PATENT DOCUMENTS

| DE | 738286 | * | 8/1943 |
| EP | 0 707 892 A1 | | 4/1996 |
| EP | 0 709 136 A1 | | 5/1996 |
| SU | 1462155 A | * | 2/1989 |
| WO | WO 95/02456 A | | 1/1995 |

* cited by examiner

*Primary Examiner*—Thomas P. Noland
(74) *Attorney, Agent, or Firm*—Ropes & Gray LLP

(57) ABSTRACT

The invention, in various embodiments, provides systems, methods and devices relating to processing a sample. A vessel is described for containing a sample. The vessel includes a reversibly sealable chamber for containing the sample which has a flexible portion to allow the vessel to deform nondestructively in response to a mechanical impact to fragment the sample. In certain embodiments the vessel may include a port for reversibly engaging with a second vessel to enable transfer of material between the two vessels while maintaining a barrier between the sample and an external environment. The vessel may be exposed to mechanical impacts of various energies and at various temperatures, and the internal surface of the structural barrier of the vessel may be treated with various chemical agents to maintain integrity of the sample.

44 Claims, 13 Drawing Sheets

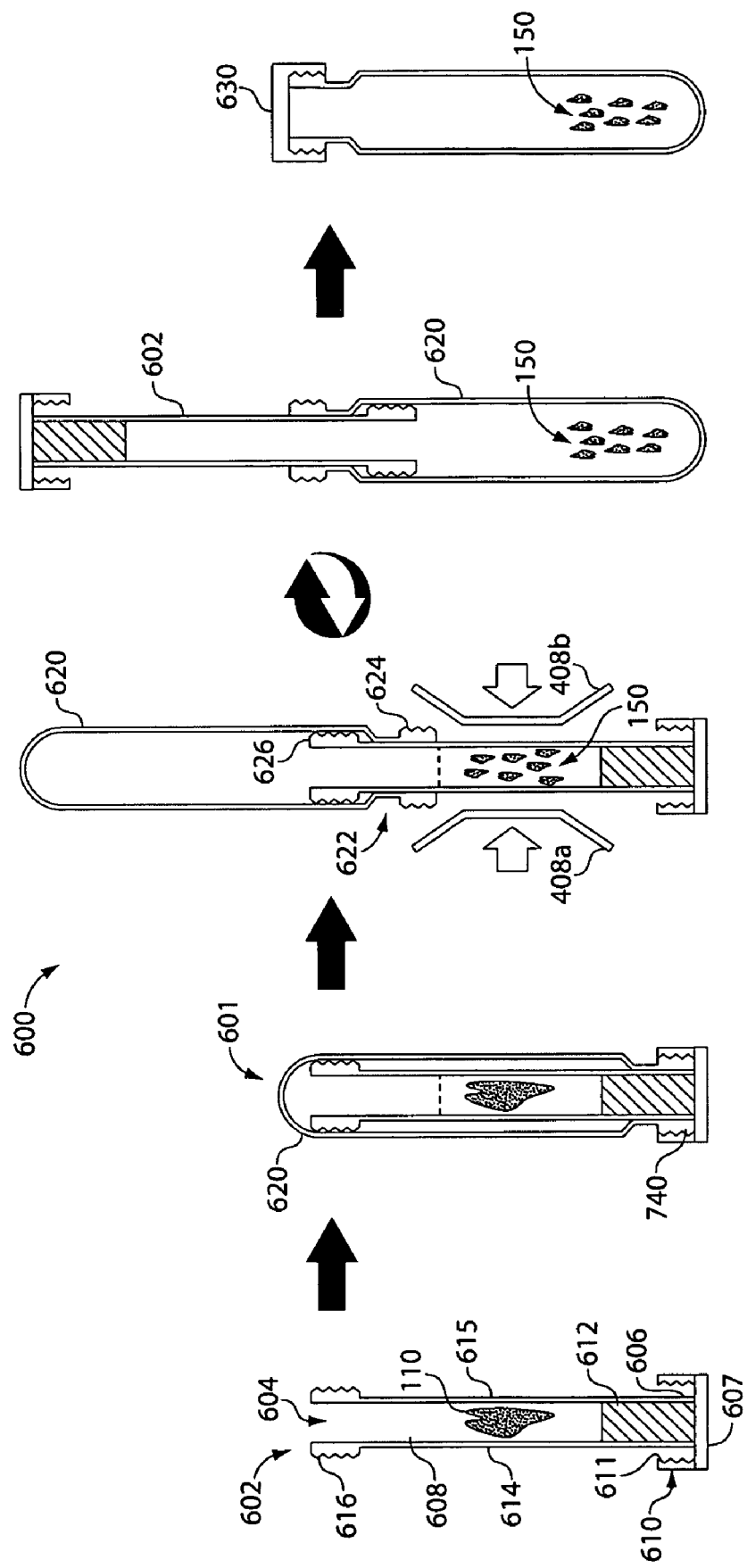

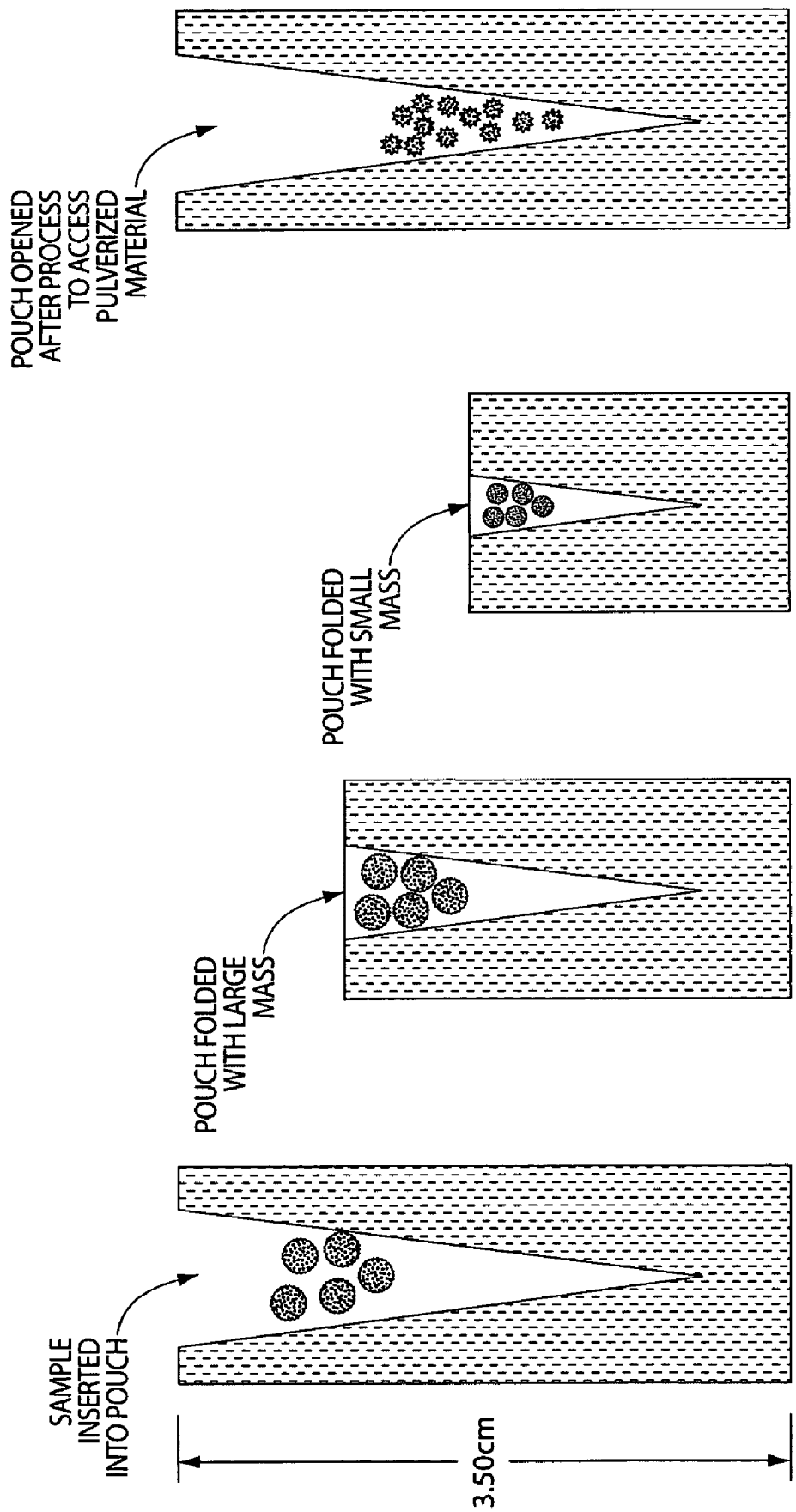

APPARATUS AND METHODS FOR SAMPLE PREPARATION

REFERENCE TO RELATED APPLICATION

This application claims priority to U.S. provisional application Ser. No. 60/528,069, filed Dec. 8, 2003, the disclosure of which is hereby incorporated by reference in its entirety.

FIELD OF THE INVENTION

The invention generally relates to systems, methods and devices for preparing and processing samples. More specifically, in various embodiments, the invention relates to pulverizing and/or fragmenting samples to ready them for analysis.

BACKGROUND

A first step in sample analysis typically involves collecting the sample. For example, a first step in a biological analysis such as RNA gene expression profiling or protein biomarker profiling is to collect a particular sample so that its biochemical constituents can be analyzed. However, prior to analysis, a solid sample specimen, typically, is prepared by deconstructing it into a plurality of smaller fragments of the specimen to enable more accurate analysis.

Recently, downstream analytical processing of samples has undergone significant improvements, including with regard to sensitivity, throughput and like. Due to these significant improvements in downstream processes, deficiencies in upstream sample collection and preparation have become more apparent. One upstream processing enhancement has been the ultrasonic systems and methods for treating a sample described in co-pending, co-owned U.S. patent application Ser. No. 10/777,014, entitled Apparatus and Methods for Controlling Sonic Treatment," the entire disclosure of which is incorporated by reference.

A challenge of sample preparation is that the types of samples are diverse. For example, samples may be biological, non-biological or a combination thereof. They may be from animals or plants. Samples may include, without limitation, cells, tissues, organelles, bones, seeds, chemical compounds, minerals, metals, or any other material for which analysis is desired.

Sample preparation is particularly challenging for solid biological samples, such as tissue samples. Physical and/or chemical approaches are often employed to disrupt and homogenize the solid sample for biochemical extraction. While appearing deceptively simple, transitioning a sample of biologically active tissue, for example, on the order of 1 gram, to a plurality of biomolecules that are stabilized and isolated in an appropriate analytical solution is exceedingly complex, very difficult to control, and prone to introduction of errors and/or sample constituent degradation.

Another challenge associated with sample preparation relates to the lability of the target molecules. For some applications, an overriding criterion is to retain the native biochemical environment prior to sample collection and throughout the extraction process, without perturbing the biochemical constituents to be analyzed. For example, RNases are extremely robust and may significantly degrade the mRNA profile of a tissue sample if the RNases are not immediately stabilized (typically thermal or chemical inactivation) at the time of tissue collection and during sample processing or homogenization. Often, to minimize perturbation of the biochemical profile of the sample, the tissue is flash-frozen (e.g., via direct immersion of the sample following procurement in liquid nitrogen) and stored at cryogenic temperatures (e.g., $-80°$ C. or lower), which inhibits degradative processes.

Conventionally, once a sample is stabilized from thermal and/or chemical degradation, it is pulverized in liquid nitrogen at a temperature of about $-196°$ C., for example, using a mortar and pestle. Other pulverizing systems available include a rotor-stator (polytron) and a bead-beater apparatus, which do not operate at cryogenic temperatures. In a typical example, a frozen specimen having a volume of approximately 1 cm$^3$ may be fragmented into a plurality of solid fragments each having a volume of approximately 100 um$^3$ or less.

Prior art approaches for performing such fragmentation suffer from many drawbacks. One such drawback is that liquid nitrogen is difficult and hazardous to work with. Another drawback is that prior art approaches can be slow and tedious. A further drawback is they involve direct contact between the sample and the fragmenting agents. For example, the sample, typically, is not contained during fragmentation causing portions of the sample to be deposited on the fragmenting devices in a non-recoverable manner. This, in turn, causes reduced sample recovery and extensive apparatus cleaning between operating cycles. Also, such deposits cause increased operator exposure to potentially hazardous samples, and/or the sample may be degraded by enzymes, bacteria, fungi, or other external contaminants.

Another challenge to sample preparation is maintaining the sample at an appropriate temperature. A disadvantage of the direct contact prior art devices, particularly the automated prior art devices, is that the sample may become sufficiently heated to cause the sample to degrade. This disadvantage is accentuated by sample fragmentation due to increased thermo-sensitivity resulting from increased surface area. Thawing also makes it difficult to transfer sample particles to a vessel for further processing. Another drawback is that conventional techniques have size range limitations. For example, a high percentage of a 25-mg sample would be lost in a 5-ml bead-beating system, causing unacceptably low sample recovery.

Accordingly, there is a need for an improved approach to preparing samples for further analysis.

SUMMARY OF THE INVENTION

The invention addresses the deficiencies of the prior art by providing, in various embodiments, systems, methods and devices for collecting, stabilizing, fragmenting and/or analyzing samples. As described above, analysis of biological and non-biological sample specimens often begins with collection of a sample of relatively large size. Before the constituents of such a sample can be effectively analyzed, the sample, preferably, is fragmented into a plurality of smaller specimens. Such smaller specimens can then be stored, analyzed, or further processed.

A sample may be any material. Exemplary samples include, but are not limited to, bones, teeth, seeds, plants, pathological or non-pathological animal tissue (e.g., muscle, liver, kidney, lung, brain, pancreas, prostate, ovary, breast, etc.), tumor tissue, rocks, mineral samples, tree bark, and/or food products. Exemplary constituents include, but are not limited to, nucleic acids, amino acids, polypeptides, bacteria, viruses, fungi, spores, small organic molecules, small inorganic molecules, metals, minerals, ores, and the like. The sample may be relatively soft, such as a tissue sample, may be relatively hard, such as a bone or mineral sample, and may include sharp knife-like edges and/or sharp needle-like points.

In one aspect, the invention provides a sample vessel for containing a sample. According to one embodiment, the sample vessel includes a chamber portion and a port portion. According to one feature, the chamber portion provides a structural barrier between the sample and an external environment. According to another feature, the barrier maintains the sample in a sterile environment. In one embodiment, the sample vessel is formed from a film material. According to one configuration, the film material is formed into a bag for containing the sample. The bag may be formed by folding a single sheet of the film and bonding it together on at least two sides. Alternatively, the bag may be formed from two sheets of film bonded together on at least 3 sides. In other configurations, the vessel is entirely, or includes portions that are, injection molded. In various embodiments, the sample vessel is formed, at least in part, from a polyimide, polysulfone, liquid crystal polymer, fluorinated polymer, and/or other like material. According to one embodiment, the bag is formed from one or more sheets of Kapton™ material (part number 150FN019 available from Dupont).

According to one feature, the sample vessel includes an aperture of any type suitable port for introducing and/or removing a sample and/or other materials from the chamber. In various configurations, the port is formed from a substantially rigid, substantially hard, and substantially non-deformable material, such a polypropylene or other suitable polymer plastic. Preferably, the port includes a hub fitting and a cap or cover for snap, pressure, screw, or other reversible sealing mating with the hub fitting to provide an additional barrier between the sample and an external environment. In some embodiments, the port is sized and shaped for mating with a second vessel for transferring the sample and/or other materials from the sample vessel to the second vessel. In other configurations, the port may configured for reversibly mating with a syringe for injecting and/or removing the sample and/or other materials into or out of, respectively, the sample vessel. According to one such configuration, the port is configured for conventional needleless mating with a syringe, for example, such as the needleless ports employed for transfer of blood products. In another such configuration, the port includes a diaphragm for resealable puncture by a syringe needle. In some implementations, a single aperture serves as the aperture for mating with the transfer container and the aperture for introducing the sample. In other embodiments, separate apertures are employed.

In one embodiment, the sample vessel includes a portion flexible enough to deform nondestructively (e.g., without experiencing cracking, tearing, ripping or other degradation in structural integrity), or in some embodiments substantially nondestructively, in response to a mechanical impact sufficient to fragment the particular sample contained within the sample vessel. According to one feature, subsequent to the mechanical impact, the sample vessel continues to maintain sufficient structural integrity to continue to separate the sample from the external environment. In one embodiment, the vessel continues to maintain the sample in sterile isolation from the external environment. According to various implementations, the mechanical impact may have an impact energy transfer of greater than or equal to about 1 Joule, 2 Joules, 3, Joules, 4 Joules, 5 Joules, 6 Joules, 7 Joules, 8 Joules, 9 Joules, or 10 Joules. According to one implementation, the mechanical impact may occur with the sample at cryogenic temperatures below about −20° C., −30° C., −40° C., −50° C., −60° C., and/or −70° C. In some implementations, the exposure to the mechanical impact may occur with the sample at cryogenic temperatures between about −80° C. and about −196° C. According to another feature, the vessel is for single use. According to another feature, the vessel may be substantially evacuated.

Depending on the mechanical properties of the sample (e.g., relatively hard, relatively soft, forms sharp or pointed shards when fragmented, etc.) and the temperature at which fragmentation is to occur, various materials may be suitable for the vessel. For example, a brain sample may require a particular film layer (e.g., 1 mil). Alternatively, a bone, seed, or rock sample, which may have sharp and or pointed features, may require a thicker film layer (e.g., 4 mil), an additional reinforcement layer, for example, of a non-woven polymer material, such as Tyvek™ (available from Dupont), reinforcement by woven or non-woven material, or other suitable reinforcement.

In various embodiments, the sample vessel is formed from a range of materials and a range of wall thicknesses to produce sample vessels appropriate for a variety of uses. For example, the sample vessel may be constructed from materials compatible for use at the above described cryogenic temperatures, as well as materials compatible for use only at non-cryogenic temperatures, such as room temperature and temperatures above the freezing point of water. By way of further example, the one or more walls of the vessel may be approximately 0.5-5 mil thick. Exemplary wall thicknesses include, but are not limited to, about 0.75 mil, 1 mil, 1.25 mil, 1.5 mil, 1.75 ml, 2 mil, 2.25 mil, 2.5 mil, 2.75 mil, 3 mil, 3.25 mil, 3.5 mil, 3.75 mil, and 4 mil.

According to some configurations, the sample vessel includes a substrate having a chamber for containing the sample formed thereon (e.g., a blister pack), wherein the chamber includes a portion flexible enough to nondestructively deform in response to a mechanical impact sufficient to fragment the sample contained within the chamber. In other configurations, the sample vessel includes one or more resiliently flexible walls.

According to some embodiments, the sample vessel includes at least two substantially rigid walls connected along their perimeters by one or more walls flexible enough to nondestructively deform sufficiently to allow the at least two substantially rigid walls to come together and contact each other with sufficient force to fragment the sample in response to a mechanical impact on at least one of the substantially rigid walls. In one implementation, the flexible walls are formed as accordion-like structures that fold along preformed creases in response to the mechanical impact.

In various embodiments, the sample vessel is sized and shaped for insertion into and functional interoperation with a mechanical impact providing device. In other embodiments, the sample vessel is also or alternatively sized and shaped for insertion into and functional interoperation with a sample preparation device for providing focused acoustic energy to the sample contained within the vessel for performing any one of: cooling; heating; fluidizing; mixing; stirring, disrupting, increasing permeability of a component of, enhancing a reaction of, sterilizing; and/or further fragmenting the sample. Such a sample preparation device is described in co-pending, co-owned U.S. patent application Ser. No. 10/777,014, entitled Apparatus and Methods for Controlling Sonic Treatment," the entire disclosure of which is incorporated by reference above.

In one embodiment, the vessel includes a mechanical, optical, and/or electronic security feature configured for interacting with a corresponding security feature on the mechanical impact providing device and/or the acoustic energy providing device, without which interaction, the mechanical impact providing device, and/or the acoustic energy providing device, respectively, will not function.

According to another aspect, the invention provides a kit including a sample vessel having any of the above described features, and a second vessel for mating with the sample vessel as described above. In one embodiment, the kit includes a suitable agent, reagent, buffer or the like for combining with the sample subsequent to fragmentation. According to one feature of this embodiment, the agent, reagent, buffer or the like is prefilled into the second vessel. According to another feature of this embodiment, the second vessel includes a barrier for maintaining the agent, reagent, buffer or the like separated from the chamber of the sample vessel until after fragmentation of the sample. In one embodiment, the barrier is broken by rotating or otherwise manipulating the sample vessel relative to the second vessel, to enable the agent, reagent, buffer or other material to fall, flow and/or be funneled into the sample vessel, or to enable the fragmented sample to fall into the second vessel.

According to another aspect, the invention is directed to a device for providing a mechanical impact to a sample vessel. In one embodiment, the mechanical impact device includes a base, a holder into which the vessel can be interfitted, and at least one impact surface for impacting the sample vessel. The impact surface can be driven, for example, by a hammer, solenoid, pneumatically actuated device, hydraulically actuated device, gravity actuated device, or any other suitable mechanism. According to one embodiment, the device includes a processor for controlling operation of the at least solenoid. According to one feature, the mechanical impact device includes a user-adjustable control for adjusting the impact force provided by the at least one solenoid. The user-interface may also include a temperature adjustment for selecting a temperature at which the impact providing device is to be maintained. According to another feature, the mechanical impact device includes a chamber/well for receiving an immersion chiller probe for maintaining at least the portion of the device containing the sample vessel at a lowered temperature to help maintain the sample at a suitable temperature to avoid sample degradation. According to another feature, other portions of the device, particularly those contacting a work surface on which the device may be placed, are maintained near or at room temperature. According to a further feature, the mechanical impact device includes a mechanical, optical and/or electronic security feature configured to interact with a corresponding security feature on the sample vessel, without which interaction, the mechanical impact providing device will not function.

According to another aspect, the invention is directed to a system for fragmenting a sample specimen, the system including a sample vessel for containing a sample specimen, and a mechanical impact providing device for receiving the sample vessel into an impact zone. In one embodiment, the vessel includes a portion flexible enough to deform nondestructively in response to a mechanical impact from the mechanical impact providing device sufficient to fragment a sample specimen contained within the sample vessel into a plurality of smaller sample specimens.

According to a further aspect, the invention provides a method for preparing a sample for analysis, storage or further processing. The method includes the steps of, placing a sample into a sample vessel, applying a mechanical impact to an external surface of at least a portion of the sample vessel having sufficient force to fragment the particular sample, while maintaining structural integrity of the enclosed vessel during application of the mechanical force. According to one feature, the method includes maintaining the sample at a temperature below about −20° C., −30° C., −40° C., −50° C., −60° C., and/or −70° C. during application of the mechanical force. According to another feature, the method includes maintaining the sample at a temperature between about −80° C. and about −196° C. during application of the mechanical force. According to a further feature, the method includes storing the sample in the sample vessel subsequent to fragmentation for future analysis.

In an alternative embodiment, the impact providing device operates at or about room temperature. However, the impact providing device operates quickly enough so that the transient exposure to the impact surfaces do not substantially warm the sample. This is also the case where the sample, itself, is maintained at room or near room temperature. In various embodiments, the impact providing device may provide elements for heating or cooling the sample prior or subsequent to fragmenting it.

According to one process, the method includes transferring the sample from the sample vessel to a mated second vessel subsequent to fragmentation. According to various embodiments, the method includes subjecting the sample to a focused acoustic field while contained in the sample or second vessel, subsequent to applying the mechanical impact.

According to an additional aspect, the invention is directed to systems and methods for processing a sample. According to one embodiment, the systems and methods include employing an automated vessel handling robot for retrieving a sample vessel of the type described herein from a storage location, providing it to an impact providing device for fragmenting the sample, inverting the sample vessel to transfer the fragmented sample into a second vessel, adding an appropriate agent, reagent, buffer or other material, as desired, to the second vessel, providing the vessel to a device for providing focused acoustic energy to the sample for homogenization and/or extraction, and placing the homogenized sample in a storage location. The storage location from which the sample vessel is retrieved and the storage location to which the homogenized sample is placed for storage may or may not be the same storage location. Additionally, storage may or may not occur at cryogenic temperatures. Ultrasonic processes of the type employed on the second vessel are described in U.S. patent application Ser. No. 10/777,014, the entire content of which is incorporated above by reference. According to a variation of this aspect of the invention, the sample is not transferred to a second vessel. Instead the sample vessel is used for the entire process, including the acoustic treatment of the sample, and/or other downstream processes, including centrifugation for spinning down particulates in the sample.

Additional systems, methods, devices, features and advantages of the invention will be discussed below with respect to the illustrative embodiments.

BRIEF DESCRIPTION OF THE DRAWINGS

The invention may be better understood by referring to the following description of illustrative embodiments, taken in conjunction with the accompanying drawings, in which like reference designations refer to like components and depictions components are not necessarily drawn to scale.

FIGS. 6A-6E show a flow diagram depicting a sample preparation process employing a vessel assembly according to an alternative illustrative embodiment of the invention.

FIGS. 14A-14D provides a conceptual flow diagram depicting a vessel of the invention employed in an experimental example using brewers yeast.

DESCRIPTION OF ILLUSTRATIVE EMBODIMENTS

As described above in summary, the invention provides, in various embodiments, systems, methods and devices for collecting, stabilizing, pulverizing, fragmenting and/or analyzing biological and non-biological sample specimens. Before constituents of such a sample specimen can be effectively analyzed, the sample specimen, preferably, is fragmented into a plurality of smaller specimens. Such smaller specimens can then be stored, analyzed, or further processed, as desired.

Figure 1:
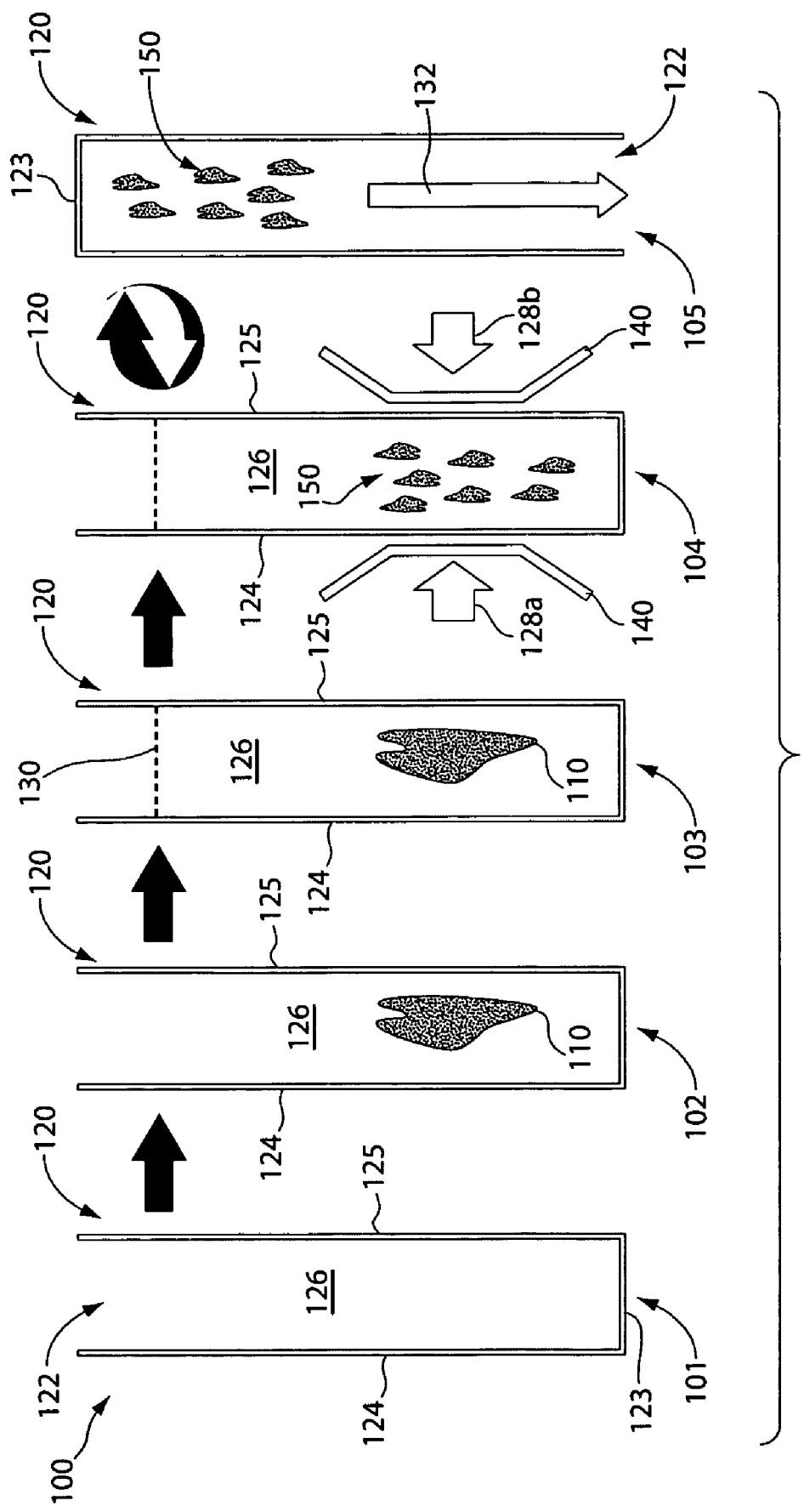
FIG. 1 is a schematic flow diagram of a sample preparation process using a vessel including a portion flexible enough to deform nondestructively in response to a mechanical impact sufficient to fragment a sample contained within the vessel, according to an illustrative embodiment of the invention.

FIG. 1 is a flow diagram depicting a sample specimen fragmentation process 100 according to an illustrative embodiment of the invention. As shown, in step 101, the process 100 provides a vessel 120. The vessel 120 includes a bottom 123 and one or more side walls 124 and 125 forming a chamber 126. In the illustrative embodiment, the top 122 of the vessel 120 is shown as open in steps 101 and 102. However, as shown in step 103, in preferred embodiments, subsequent to introduction of a sample, such as the sample 126, the top 122 closed with a protective seal 130. The protective seal 130 may be, for example, a mating cover, snap cap, screw top or stopper sized and shaped to interfit with the top 122. However, in other illustrative embodiments, barrier 130 may include, without limitation, any suitable structure for sealing the top 122 closed, including, without limitation, a structure for heat sealing, crimping, clipping, and/or gluing the top 122 closed. According to the illustrative embodiment, the interior surfaces of the vessel 120 is coated with a material for facilitating heat sealing the top portion 122 to a fitting (described in more detail below with respect to FIGS. 2A, 2B, 8 and 9), into which a stopper may be screwed or otherwise interfitted. By way of example, the interior surfaces of the vessel 120 may be coated with a layer of FEP (fluorinated ethylene propylene).

According to the illustrative embodiment, the vessel 120 in combination with the protective seal 130 provide a barrier for structurally isolating the sample 110 from an external environment. According to one illustrative feature, the vessel 120 maintains the sample 110 in a sterile environment.

As shown at step 104, subsequent to loading the sample specimen 110 into the chamber 126, the vessel 120 is installed into a mechanical impact providing device. The mechanical impact providing device includes at least one impact providing surface driven for example by a hammer, solenoid piston, pneumatically actuated device, hydraulically actuated device, gravity actuated device, or any other suitable mechanism (e.g., the solenoids 140). As indicated by the arrows 128a and 128b, the solenoids 140 impact at least a portion of the side walls 124 and 125 at high velocity. The mechanical impact from the solenoids provides a force sufficient to disrupt the macro-structure of the sample specimen 110, and fragment it into a plurality of specimens 150 between interior surfaces of the side walls 124 and 125. Illustratively, the impact force is between about 10 Joules and about 25 Joules. In other illustrative embodiments, the impact force may be greater than about 10 Joules, 12 Joules, 14, Joules, 16 Joules, 18 Joules, 20 Joules, 22 Joules or 25 Joules. The impact, in one example, reduces the size of the sample to fragments 150 of less than about 1 mm in the greatest dimension. In a preferred embodiment, the solenoids 140 may be caused to contact the vessel 120 more than one time to achieve the desired sample fragmentation. For example, the vessel 120 be contacted 1, 2, 3, 4, 5, or more than 5 times. When a sample is contacted multiple times, the magnitude of each impact force may be the same or may vary.

Although FIG. 1 conceptually shows two solenoids 140, in alternative embodiments, the impact providing device may include a single moving portion having a first surface actuated to fragment the sample specimen 110 against a stationary second surface.

According to the illustrative embodiment, the vessel 120 includes at least one portion flexible enough to deform nondestructively (e.g., without experiencing cracking, tearing, ripping or other degradation in structural integrity), or in some embodiments substantially nondestructively, in response to the mechanical impact from the solenoid 140. According to one illustrative feature, subsequent to the mechanical impact, the vessel 120 continues to maintain sufficient structural integrity to continue to isolate or substantially isolate the sample from the external environment, including the impact surfaces of the solenoid 140. Preferably, the vessel 120 continues to maintain the sample 110 in sterile isolation and structurally separated from the external environment subsequent to the mechanical impact.

As shown in the illustrative embodiment of FIG. 1 at step 104, one or both of the side walls 124 and 125 are deformable under the above described conditions. Also according to the illustrative embodiment of FIG. 1, the sample is maintained at a temperature below about −20° C., −30° C., −40° C., −50° C., −60° C., and/or −70° C. during application of the mechanical impact. In some implementations, the exposure to the mechanical impact occurs with the sample at between about −80° C. and about −196° C. According to the illustrative embodiment, the deformable portion of the vessel 120 remains nondestructably deformable at such temperatures. According to another feature, the vessel 120, with the barrier 130 installed, may be substantially evacuated.

Preferably, at least the interior surfaces of the vessel 120 are fabricated from a material that is substantially inert, and thus does not react (e.g., chemically or biochemically react) with the sample 110. According to the illustrative embodiment, at least the deformable portion of the vessel 120 is fabricated from, or otherwise includes, a Kapton™ (part number 150FN019 available from Dupont) or other polyimide film.

According to the illustrative embodiment, the interior surfaces of the vessel are coated with one or more agents useful in maintaining integrity of the sample, such as DNase inhibitors, RNase inhibitors, protease inhibitors, anti-coagulents, anti-bacterial agents, anti-fungal agents, and/or chelating agents (e.g., EDTA, EGTA), glycerol, and/or the like. In some illustrative embodiments, the interior of the vessel is coated with a single agent, whereas in other illustrative embodiments, it is coated with multiple agents. These agent(s) may be used to coat the interior of the vessel 120, regardless of the particular vessel material and regardless of whether the vessel 120 includes a layer of FEP or other heat-sealable material.

As shown at 105, the pulverized sample pieces 130 may be further processed or stored for further processing in the vessel 120, or as indicated by the arrow 132, may be transferred to another vessel for further processing. Further processing may include, without limitation, exposure to a focused acoustic energy source to cause, for example: sample cooling; heating; homogenizing, fluidizing; mixing; stirring; disrupting; increasing permeability of a component of; enhancing a reaction of; sterilizing; and/or further sample fragmenting. Such further processing is described in co-pending, co-owned U.S. patent application Ser. No. 10,777,014, the entire disclosure of which is incorporated by reference above. Further processing may also include any detection, identification, measurement and/or other analysis performed on the sample.

According to another illustrative embodiment, the vessel 120 includes a mechanical, optical, and/or electronic security feature, such as an interlocking mechanical feature, radio frequency identification code, or barcode configured for interacting with a corresponding security feature on the mechanical impact providing device (described below in detail with regard to FIG. 4) and/or the acoustic energy providing device described in detail in patent application Ser. No. 10,777,0140, without which interaction, the mechanical impact providing device, and/or the acoustic energy providing device, respectively, will not function.

The exterior of the vessel 120 may also include markings, for example, by printing or other mechanism for various purposes such as bar-coding, user guidance and instruction, and to mark the preferred sample location or impact target area for efficient processing. Exterior markings can occur at any point during sample handling and processing, and may occur at multiple points during sample handling. Additionally, when sample handling involves transfer of the sample between two or more different vessels, such as discussed below with regard to FIG. 2A, the one or both vessels may be marked. Marking can include barcodes (optical), RFID (electrical), punched holes (mechanical) or the like.

Figure 2A:
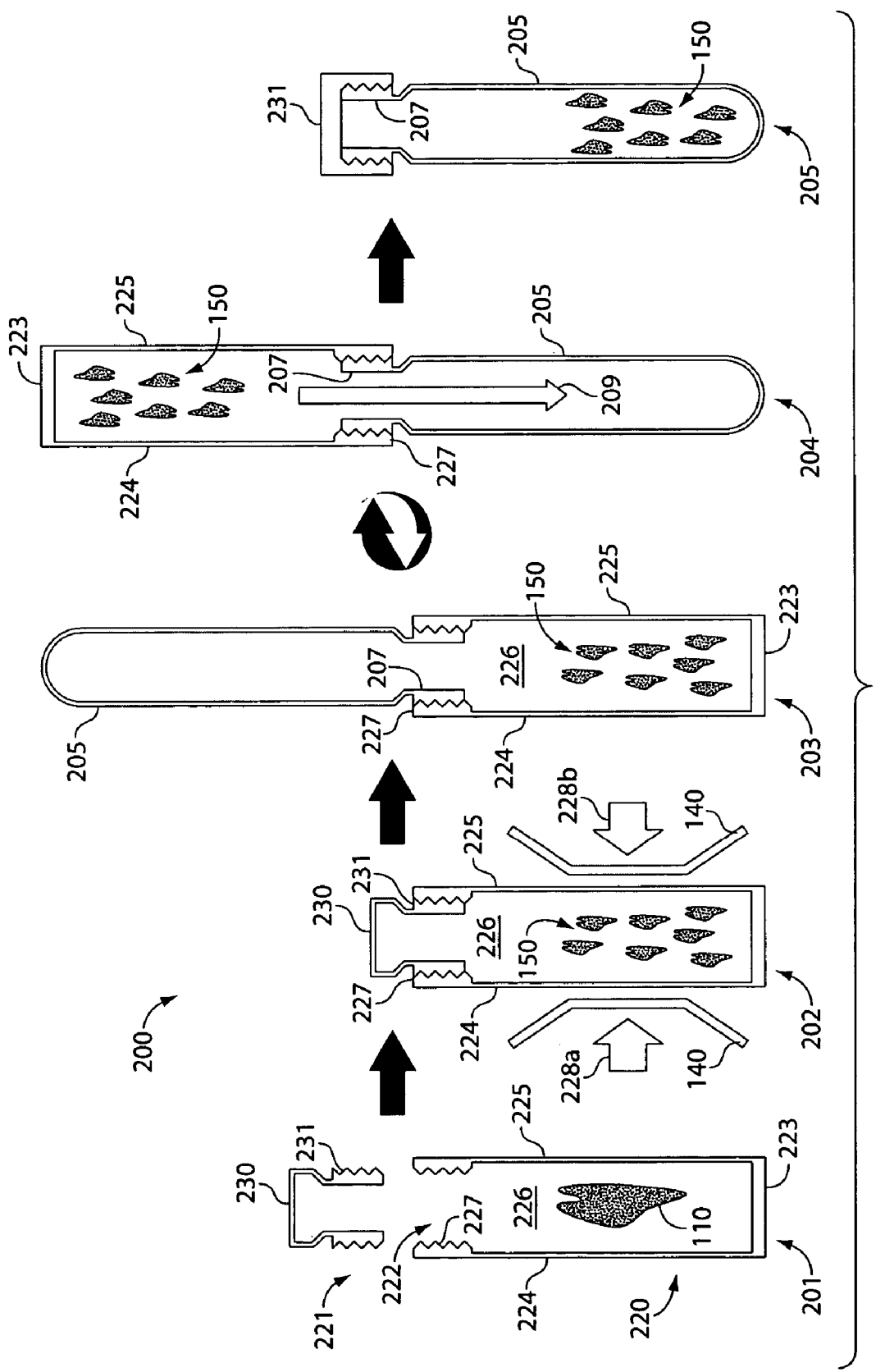
FIG. 2A is a schematic flow diagram of a sample preparation process using a vessel of the type depicted in FIG. 1 in conjunction with another vessel for further processing of the sample, according to one illustrative embodiment of the invention.

FIG. 2A is a schematic flow diagram of a sample preparation process 200 using a vessel assembly 221, including a vessel 220 of the type depicted at 120 in FIG. 1, in conjunction with another vessel 205 for further processing the sample 110, according to a illustrative embodiment of the invention. One particular non-limiting example of a vessel 205 is a borosilicate glass culture tube (screw-cap) with a round bottom, 16×100 mm (Fisher, p/n 14-962-26F, Pittsburg, Pa.).

In a similar fashion to the vessel 120, the vessel 220 includes a bottom 223 and one or more side walls 224 and 225 forming a chamber 226. In the illustrative embodiment, the vessel 220 includes a reversibly sealable top 222. More particularly, the vessel includes a threaded fitting 227 located within and affixed to the top 222. The vessel assembly 221 also includes a mating cover or stopper 230 including threads 231 sized and shaped to interfit with the threaded fitting 227. With the stopper 230 installed into threaded fitting 227, the vessel 220 provides, in some embodiments, a barrier for structurally isolating the sample 110 from an external environment, and optionally maintaining the sample 110 in a sterile environment.

According to the illustrative embodiment of FIG. 2A, the threaded fitting 227 is heat bonded to the interior surfaces of the top 222 of the vessel 220. However, in alternative embodiments, the threaded fitting 227 may be clipped, crimped, shrink wrapped, glued or otherwise affixed within the top 222. According to the illustrative embodiment, the interior surfaces of the top 222 of the vessel 220 is coated with, for example, FEP (fluorinated ethylene propylene), for facilitating heat sealing the top portion 122 to the threaded fitting 227.

As shown at step 202, subsequent to loading the sample specimen 110 into the chamber 226 and installing the stopper 230, the vessel 120 is installed into a mechanical impact providing device. As in the case of the process of FIG. 1, the mechanical impact providing device includes one or more solenoids 140. As indicated by the arrows 228a and 228b, the solenoids 140 contact at least a portion of the side walls 224 and 225 at high velocity. The mechanical impact from the solenoids provides a force sufficient to disrupt the macro-structure of the sample specimen 110, and fragment it into a plurality of specimens 150 between interior surfaces of the side walls 224 and 225.

As in the case of the vessel 120 of FIG. 1, the vessel 220 includes at least one portion flexible enough to deform nondestructively (e.g., without experiencing cracking, tearing, ripping or other degradation in structural integrity), or in some embodiments substantially nondestructively, in response to the mechanical impact from the solenoids 140. As also in the case of the vessel 120, subsequent to the mechanical impact, the vessel 220 continues to maintain sufficient structural integrity to continue to isolate or substantially isolate the sample 150 from the external environment, including the impact surfaces of the solenoids 140. Preferably, the vessel 220 continues to maintain the sample 110 in structurally separated from the external environment subsequent to the mechanical impact.

As shown in the illustrative embodiment of FIG. 2A at step 202, one or both of the side walls 224 and 225 are deformable under the above described conditions. As in the case of the illustrative embodiment of FIG. 1, the exposure to the mechanical impact occurs at temperatures below about −20° C., −30° C., −40° C., −50° C., −60° C., and/or −70° C. In some implementations, the exposure to the mechanical impact occurs at between about −80° C. and about −196° C. As in the case of the illustrative embodiment of FIG. 1, the deformable portion of the vessel 220 remains nondestructably deformable at such temperatures. The vessel 220, with the stopper 230 installed, may be substantially evacuated.

As in the illustrative vessel 120, at least the interior surfaces of the vessel 220 are fabricated from a material that is substantially inert, and thus does not react (e.g., chemically or biochemically react) with the sample 110. Illustrively, at least the deformable portion of the vessel 220 is fabricated from, or otherwise includes, a Kapton™ (part umber 150FN019 available from n) or other polyimide film.

In a similar fashion to the illustrative vessel 120, the interior surfaces of the vessel 220 are coated with one or more agents useful in maintaining integrity of the sample, such as DNase inhibitors, RNase inhibitors, protease inhibitors, anti-coagulents, anti-bacterial agents, anti-fungal agents, chelating agents (e.g., EDTA, EGTA), glycerol and/or the like. Single or multiple agent internal wall treatments may be employed. These agent(s) may be used to treat the interior of the vessel 220, regardless of the particular vessel material and regardless of whether the vessel 220 includes a layer of FEP or other heat-sealable material.

In step 203, the threaded plug 230 is removed from the top 222 of the vessel 220, and the second vessel 205, for example, a threaded borosilicate processing tube 205 having a threaded top 207 is screwed into the threaded fitting 227. In step 204 and as indicated by the arrow 209, the sample vessel 220 is then inverted to transfer the fragmented sample specimens 150 into the processing tube 205. Transfer of the sample specimens 150 may occur by simply inverting the sample vessel 220 with respect to the processing vessel. Additionally, the sample vessel 220 may be flicked, tapped, or otherwise contacted with a mild force to facilitate transfer of the sample specimens 150 into the processing tube 205. In step 205, the vessel 220 is then unscrewed off the processing tube 205 and a cap 231 is screwed onto the processing tube 205 to maintain the sample specimens 150 structurally separated from an external environment. As described above, with respect to FIG. 1, the sample tube 205 may be stored for later processing or be immediately exposed to the further processing.

As in the case of the vessel 120, the illustrative vessel 220 may include a mechanical, optical, and/or electronic security feature, such as an interlocking mechanical feature, radio frequency identification code, or barcode configured for interacting with a corresponding security feature on the mechanical impact providing device (described below in detail with regard to FIG. 4) and/or the acoustic energy providing device described in detail in U.S. patent application Ser. No. 10,777,0140, without which interaction, the mechanical impact providing device, and/or the acoustic energy providing device, respectively, will not function.

According to one feature of the invention, the sample 110 is kept structurally separated from an external environment during the fragmentation process. According to another advantage, the vessels 120 and 220 may be a single use vessels that are discarded subsequent to the sample transfer step. According to another advantage, the impact surfaces of the mechanical force providing device are not exposed to the sample 110, and thus require no cleaning before being used again. This enables a plurality of samples to be processed in series faster and more efficiently. According to a further advantage, by maintaining the sample 110 in sterile isolation and not requiring the fragmentation device to be cleaned by the operator after each use, the likelihood of exposing the operator to the sample is reduced. The likelihood of sample contamination is also reduced.

Although in the illustrative embodiments of FIGS. 1 and 2A, the sample specimens 150 are transferred, for example, to the tube 205 for further processing and/or storage, in alternative embodiments, the vessels 120 or 220 containing the sample specimens 150 are employed for the further processing and/or storage, and no sample transfer steps 105, 203, 204 and/or 205 occur. One factor in deciding whether to carry out the transfer steps 105, 203, 204 and/or 205 may be whether the vessel 120/220 or the vessel 205 is better suited for the particular further processing and/or storage.

As described above with respect to FIG. 1, one option for further processing is exposing the sample 150 to focused acoustic energy of the type described above and in U.S. patent application Ser. No. 10,777,014. To accommodate such subsequent processing, in some illustrative embodiments, the vessels 120 and/or 220 include at least a portion that is substantially transparent to a focused acoustic wave of the type described in U.S. patent application Ser. No. 10,777,014. In other words, such portion allows the described acoustic waves to pass without significant or preferably any substantial distortion. According to one embodiment, the distortion, if any, is at least small enough to enable the processing described in U.S. patent application Ser. No. 10,777,014 to occur. According to one embodiment, the acoustically transmitting portion is located in the bottom 123/223 of the vessel. Whereas in other embodiments, it is located in at least one of the side walls 124 and 125 and/or 224 and 225.

Figure 2B:
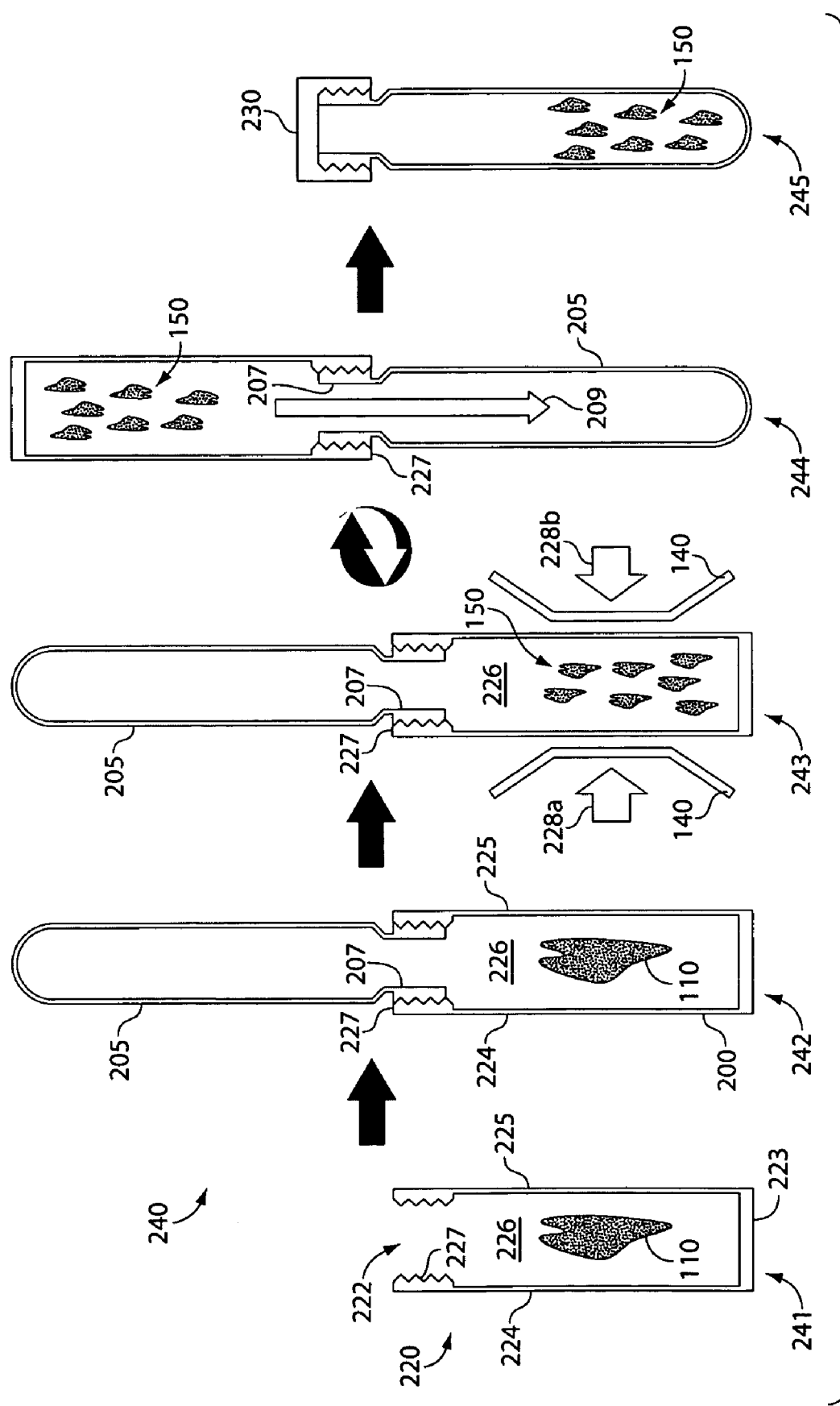
FIG. 2B is a schematic flow diagram of a sample preparation process using a vessel of the type depicted FIG. 1 in conjunction with another vessel for further processing of the sample, according to another illustrative embodiment of the invention.

FIG. 2B is a flow diagram depicting an alternative process 240 for fragmenting the sample 110 according to another illustrative embodiment of the invention. The process of FIG. 2B employs a vessel 220 and a vessel 205 identical to and having the same advantages and properties of the vessels 220 and 205 of FIG. 2A. One difference between the process 200 of FIG. 2A and the process 240 of FIG. 2B is that the process 240 does not employ the stopper 230. Instead, after the sample 110 is loaded into the chamber 226 in step 241, the vessel 205, in step 242, is screwed into the fitting 227 to connect the vessels 205 and 220 to each other. The fragmenting step 243 then proceeds in the same manner as the fragmenting step 202 of FIG. 2A. Similarly, the sample transfer step 244 and the capping step 245 proceed in the same manner as the sample transfer step 204 and the capping step 205, respectively, of FIG. 2A.

One advantage of the process 240 is that it eliminates the steps of inserting and removing the stopper 230, thus eliminating a chance for sample contamination and operator exposure to the sample. Another advantage is that the tube 205 may be used as a handle for inserting the vessel 220 into the impact providing device. It may also be used as a handle for dipping the vessel 220 into a cryogenic fluid to maintain the sample 110 at a desired cryogenic temperature during processing. A further advantage of attaching the tube 205 prior to fragmentation is that it provides additional volume, which reduces the increase in pressure due to the compression of the sample vessel 220 during fragmentation.

As discussed above and as depicted in FIGS. 2A and 2B at 203 and 242, respectively, the sample vessel 220 may be interfitted with the processing vessel 205. The processing vessel 205 may have an agent, reagent, buffer or other relevant material placed in it prior to interfitting with the vessel 220. Preferably, the processing tube 205 includes a barrier for containing the material so that it does not spill into the vessel 220 at an undesirable time. According to one feature, an operator can cause the barrier to break to release the material into the sample vessel 220 or to allow the sample 120 to be transferred to the processing vessel 205. Such transfer may be caused to occur before, after or during fragmentation. Breaking of the barrier may be caused, for example, by the fragmenting process. Breaking of the barrier may alternatively be caused by an operator rotating or otherwise manipulating the relative positions of the sample 220 and processing 205 vessels. In another illustrative embodiment, the operator squeezes the sample vessel 220 to decrease its volume sufficiently to create a pressure against and break the barrier of the processing vessel 205. Any other suitable method for breaking such a barrier may be employed.

Figure 3A:
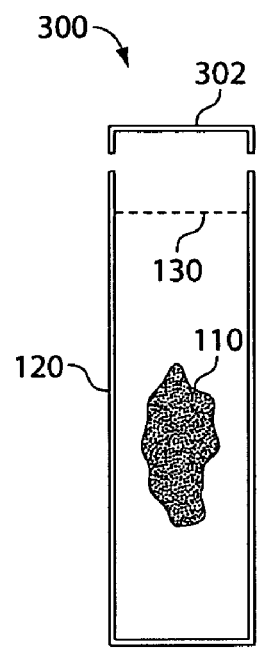
FIGS. 3A-3B depict two illustrative approaches for placing samples in and removing samples from vessels, according to various illustrative embodiments of the invention.
Figure 3B:
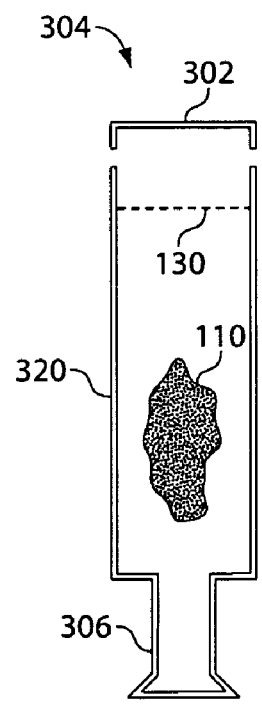

The mechanism for placing a sample 110 in and removing it from a vessel, such as the vessels 120 and 220 described above, may employ any suitable approach, including any conventional approach, such as those used for storing and administering pharmaceuticals and blood products. FIGS. 3A and 3B show two illustrative configurations for placing a sample 110 in and removing it from a vessel according to an illustrative embodiment of the invention.

More particularly, FIG. 3A shows the vessel 120 employing a single seal providing element 302 for providing the conceptually indicated environmental seal 130. As described with regard to FIGS. 1 and 2A, the seal providing element may include, without limitation, a mating cover, snap cap, screw top or stopper sized and shaped to interfit with the top of the vessel 120. Alternatively, the top of the vessel 120 may be sealed, without limitation, by crimping, heat sealing, clipping, and/or gluing. In the configuration of FIG. 3A, the sample 120 is inserted and removed by way of the single element 302. The element 302 may include a resealable diaphragm for injecting a fluid into the vessel 120 and/or for removing the sample 110 from the vessel 120 with, for example, a syringe subsequent to, for example, fluidization, mixing or stirring, as described in U.S. patent application Ser. No. 10/777,014.

FIG. 3B shows an alternative illustrative embodiment in which a vessel 320 of the invention includes two ports, a loading port 302 of the type described above with respect to FIG. 3A, and a transfer port 306. The transfer port 306 may be, for example, any conventional port employed for transferring a fluid to a from a vessel. The configuration of FIG. 3B enables a relatively large sample to be placed in the vessel 320 by way of the loading port 302, and removed subsequent to size reduction by way of the transfer port 306.

Figure 4:
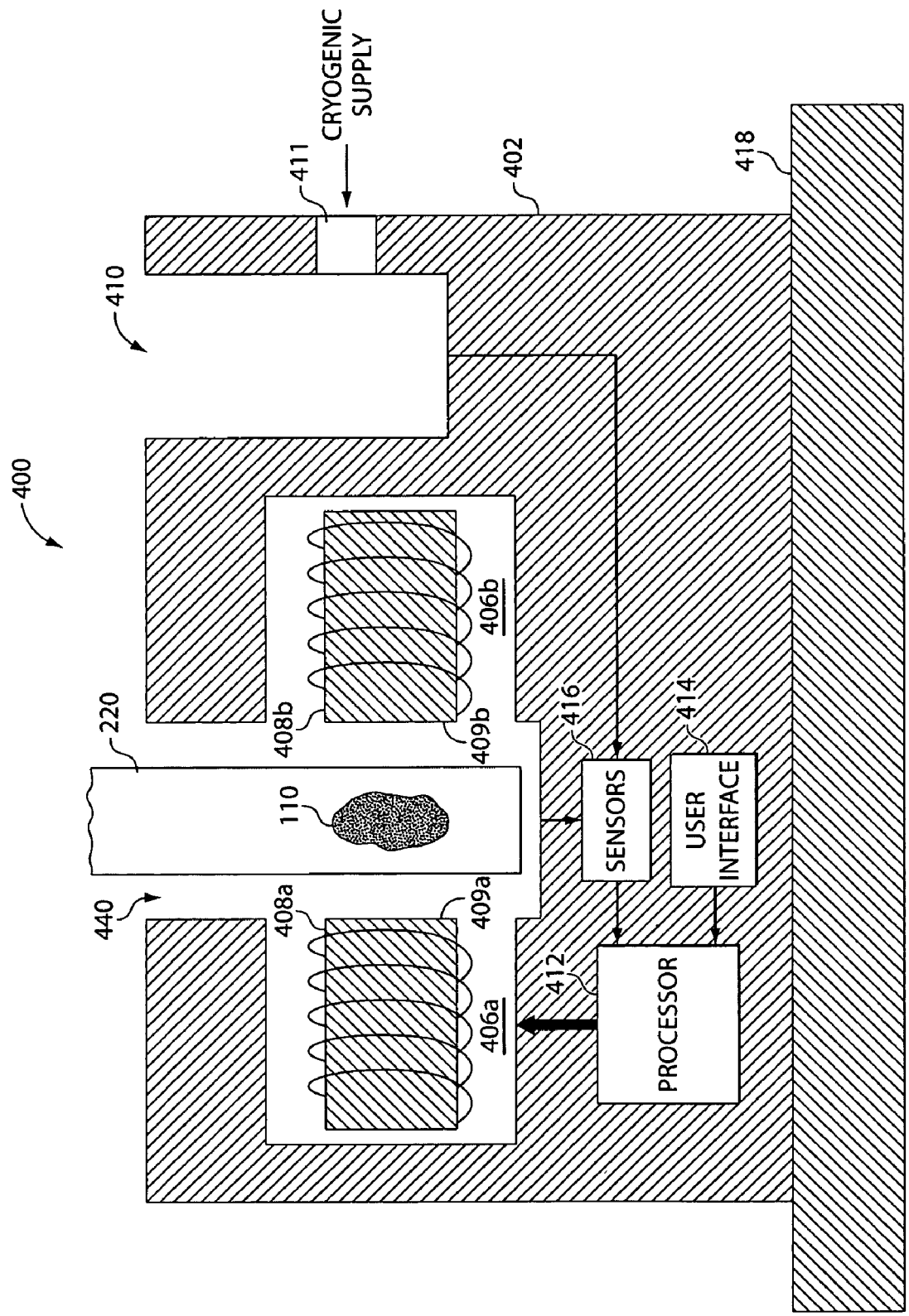
FIG. 4 is a conceptual block diagram of an impact providing device according to an illustrative embodiment of the invention.

FIG. 4, is a conceptual block diagram of an impact providing device 400 of the type which may be used with vessels, such as the vessels 120 and 220, described above with respect to FIGS. 1-3B. For illustrative purposes only, the vessel 220 of FIGS. 2A and 2B containing the sample 110 is depicted as inserted into the device 400.

As shown, the device 400 includes a housing 402. The housing 402 is preferably made of metals such as nickel, aluminum, stainless steel 18-8, and/or copper, and includes a vertically disposed cavity 404 having features of any suitable structure for receiving and stabilizing the vessel 220. More particularly, cavity 404 of the impact providing device 400 may contain a holder, tubular barrel or other features for optimally positioning the vessel 220 and/or the sample 110 with respect to the impact surfaces. The positioning feature may include a substantially rigid outer wall for providing lateral support for retaining the sample vessel 220 vertically within the cavity 404. The substantially rigid wall may include apertures for enabling the below discussed solenoids to strike the vessel 220. The positioning feature may be made, for example, from polypropylene.

The housing 402 also include two cavities 406a and 406b disposed horizontally and extending in opposite directions from the vertically disposed cavity 404. Opposing solenoids 408a and 408b are located in the horizontally extending cavities 406a and 406b, respectively. The solenoids 408a and 408b include impact surfaces 409a and 409b, respectively. Although, the device 400 is shown with two movable impact surfaces 409a and 409b, in alternative embodiments, one of the impact surfaces may be stationary (e.g., being located on a wall as opposed to a solenoid) and the other impact surface may be movable.

The impact surfaces 409a and 409b may be made, for example, from face-centered cubic (fcc) metals and their alloys, such as aluminum, stainless steel 18-8, copper, and nickel. The surfaces 409a and 409b may be a hammer/anvil design and may be chilled to below about −20° C., −30° C., −40° C., −50° C., −60° C., and/or −70° C. In some implementations, the impact surfaces 409a and 409b are chilled to between about −80° C. and about −196° C. The impact surfaces 409a and 409b may be substantially flat and parallel to each other. Alternatively, the surfaces 409a and 409b may be slightly angled relative to each other. Slightly angled surfaces tend to concentrate the sample fragments 150 at the bottom of the vessel 220. This may facilitate the fragmentation of certain samples. In such embodiments, the angle of the impact surfaces 409a and 409b may be considered a "fixture" specifically designed to align the impact surfaces with respect to the vessel 220 and/or the sample 110.

The housing 402 also includes a cavity 410 for receiving an Immersion Cooler/chiller (Thermo Neslab CC65, Portsmouth, N.H.) capable of achieving at least about −35° C. In this embodiment, a chilled probe is inserted into the cavity 410 to cause the sample 110 to be maintained at a desired cryogenic temperature. The housing 402 may also include a port 411 for receiving a supply of cryogenically cooled fluid, such as liquid Nitrogen, to achieve the same result. The housing 402 may also include a thermally insulated base 418 for reducing heat transfer between a workbench and the device 400, thus enabling the device 400 to operate with out the need for any additional insulation between it an a work surface.

The device 400 also includes a processor for controlling operational parameters of the solenoids 408a and 408b. Operational parameters include, for example, the speed, acceleration, and/or force with which the impact surfaces 409a and 409b of the solenoids 408a and 408b, respectively, are driven together. The operational parameters also include the number of times the solenoids 408a and 408b are driven together. The illustrative impact providing device 400 also includes a user interface 414. The user interface 414 enables an operator to select the solenoid operational parameters, for example, according to the particular sample, the desired degree of fragmentation (e.g., the desired size of the fragmented sample fragments), and/or the future use of the pulverized fragments. The user interface 414 may also include an actuator for initiating the impact from the solenoids 408a and 408b. Alternatively, impact is automatically initiated by the processor 412 in response to detecting that the vessel 220 has been properly inserted into the cavity 404. Thus, the device 400 may be operate in an automated (e.g., impact automatically initiated), semi-automated (e.g., operator can set operational parameters), or manual (e.g., user operates an actuator to initiate impact) mode.

The device 400 further includes sensors 416. As described above, the vessels 120 and 220 may include a mechanical, optical, and/or electronic security feature, such as an interlocking mechanical feature, radio frequency identification code, or barcode. Correspondingly, the sensors 416 may includes one or more sensors sensing an appropriate security feature from the vessels 120 and 220. In response to the sensors 416 detecting the appropriate security feature, the processor 412 enables operation of the solenoids 408a and 408b. However, according to the illustrative embodiment, in the absence of such detection, the processor does not allow the solenoids 406a and 406b to function.

The sensors 416 may also include one or more temperature sensors for detecting the temperature, for example, of the cryogenic chamber 410 or other portion of the housing 402.

Fragmentation within the device 400 may occur at any of a number of temperatures, including across a range of cryogenic temperatures. Temperature can be monitored during pulverization via the sensors 416 and adjusted, automatically by the processor 412. The temperature may also be adjusted via an operator selectable feature included in the user interface 414.

When pulverization occurs at cryogenic temperatures, condensation may form within the device 400. Such condensation can potentially interfere with electronics, such as the processor 412, that allow automation of the device 400, or with sensors within the device 400 that modulate, for example, device temperature and/or impact force, and/or with sensors that scan detect security features on the vessel 220. Accordingly, the invention, in some illustrative embodiments, circulates an inert, anhydrous gas (e.g., compressed nitrogen) throughout all or a portion of the housing 402 to reduce and/or prevent condensation in and around the electronic elements and sensors.

Although the device 400 is described as employing the solenoids 408a and 408b, other impact mechanisms may be employed, such as, a vice, hammer, solenoid, pneumatically actuated device, hydraulically actuated device, gravity actuated device, or any other suitable mechanism.

Figure 5A:
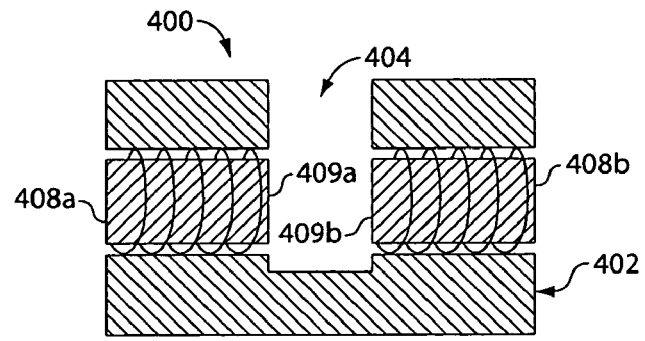
FIGS. 5A-5D show a schematic flow diagram depicting a sample preparation process using a mechanical impact providing device of the type depicted in FIG. 4, according to an illustrative embodiment of the invention.
Figure 5B:
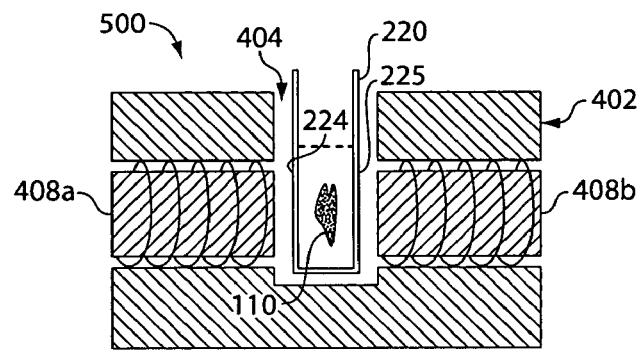
Figure 5C:
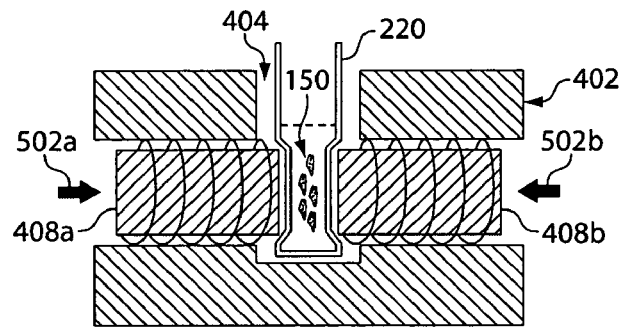

FIGS. 5A-5C show a schematic flow diagram depicting a sample preparation process using a mechanical impact providing device 400 and a vessel 220 of the type described above. In FIG. 5A, the device 500 is shown in a rest state, with the solenoids 408a and 408b retracted. In FIG. 5B, the vessel 220 including a sample 110 is interfitted into an impact zone within the chamber 404 of the device 500. In FIG. 5C, as indicated by the arrows 502a and 502b, the opposed solenoids 508a and 508b are activated, causing the surfaces 409a and 409b to impact on the walls 224 and 225, respectively, of the vessel 220. Illustratively, the vessel 220 employs one or more of the above described features to enable the vessel to nondestructively deform and allow the sample 110 to be fragmented between least a portion of the inner surfaces of the walls 224 and 225 in response to the contact by the surfaces 409a and 409b. As described above, the fragmentation of FIG. 5C may occur at cryogenic temperatures. According to the illustrative embodiment, the solenoids 408a and 408b may be fired one, two, or more times to achieve the desired degree of fragmentation.

Figure 5D:
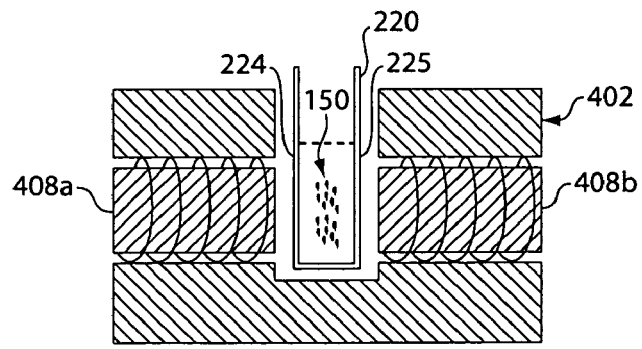

As shown in FIG. 5D, after the desired degree of fragmentation is achieved, the solenoids 408a and 408b retracted into the cavities 406a and 406b to enable removal of the sample vessel 220. Although, the vessel 220 is shown in FIG. 5D as returning to its original shape, this need not be the case. However, as described above, the vessel 220, preferably, maintains its structural integrity during the fragmentation process.

FIGS. 6A-6E provide a flow diagram 600 illustrating use of a vessel assembly 601 with the mechanical impact providing device 400 according to another illustrative embodiment of the invention. Referring to FIGS. 6A and 6B, the vessel assembly 601 includes a first vessel 602. The vessel 602 includes any or all of the features relating to nondestructive deformation described above with regard to the vessels 120 and 220. As in the case of the vessels 120 and 220, the vessel 602 includes a top 604, a closed bottom 607 and one or more side walls 614 and 615 forming a chamber 608.

The top 604 is open and includes threaded portion 616. The threaded portion 616 may be a fitting into which the end 604 interfits and is fastened, such as by heat shrinking, gluing, thermal bonding or any other suitable mechanism. Alternatively, the threaded portion 616 may be formed into the vessel 602 itself. A stopper 612 having a base 607 interfits into the bottom end 606 of the vessel 602. As in the case of the threaded portion 616, the stopper 612 may be fastened within the bottom 606 of the vessel 602 by any suitable mechanism. A wall 610 extends vertically from and circumscribes the base 607. The wall 610 includes an inner threaded portion 611.

The vessel assembly 601 also includes a second vessel 620. Referring also to FIG. 6C, the vessel 620 includes a bottom portion 622, which includes external 624 and internal 626 threads. The threads 624 and/or 626 may be formed directly on the bottom portion 622 or may be provided by a suitable fitting. Referring to FIGS. 6A and 6B, in operation, a sample 110 is introduced into the chamber 608 by way of the opening at the end 604. The stopper 612 may be sized to position the sample 110 at a particular height in the chamber 608. The vessel 620 is then fitted concentrically over the vessel 602 and rotated relative to the vessel 620 to engage the inner threads 626 of the vessel 620 with the outer threads 616 of the vessel 614. The vessel 620 is rotated relative to the vessel 602 until the threads 616 are passed and the vessel 620 slide over the vessel 602. As shown in FIG. 6B, the vessel 620 is then further rotated relative to the vessel 602 to cause the outer threads 624 on the vessel 620 to engage with the inner threads 611 on the wall 610. The two vessels may be rotated relative to each other until they are tightly screwed together. The assembly 601 may be stored and/or shipped in this configuration until further processing is desired.

As shown in FIG. 6C, at the time of further processing, the vessel 620 can be unscrewed from the wall 610, slid up the vessel 602 and rotated to cause the inner threads 626 of the vessel 620 to engage with and screw onto the outer threads 616 of the vessel 602. With the two vessels 602 and 620 so engaged, the vessel 602 may be inserted into the device 400 as discussed above to fragment the sample specimen 110 into a plurality of sample specimens 150. As shown in FIG. 6D, the assembly 601 can then be inverted to transfer the fragmented specimens 150 into the vessel 620. As shown in FIG. 6E, the vessel 602 can then be screwed off of the vessel 620 and a screw cap 630 can be inserted onto the vessel 620 to maintain the sample 150 in sterile isolation.

Advantage of the system of FIGS. 7A-6E over the system of FIGS. 2A and 2B include: the total volume of the assembly 601 is less during storage and shipping than the volume of the vessels 220 and 225, mated as shown at 243 in FIG. 2B; a label need be applied to only one vessel; and the transfer process is more rapid if pre-assembled as shown in FIG. 6B.

Figure 7:
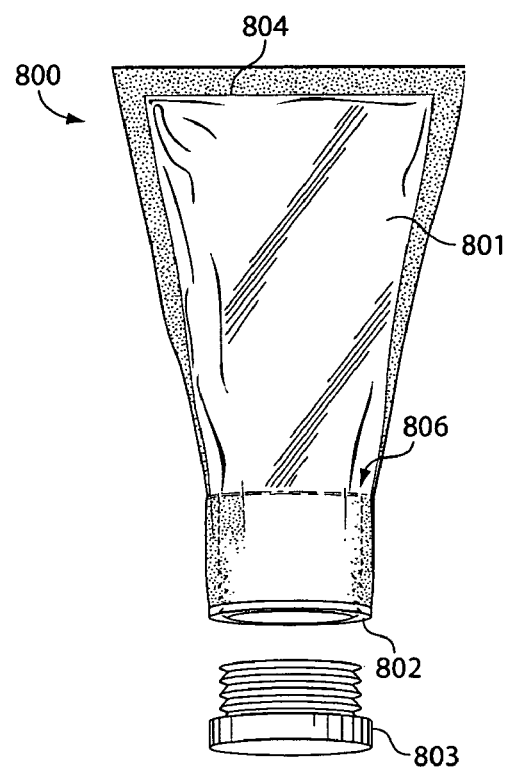
FIG. 7 depicts a sample preparation vessel according to one illustrative embodiment of the invention.

FIG. 7 is a diagram of a sample vessel 800 according to another illustrative embodiment of the invention. The vessel 800 includes one or more of the deformable characteristics as described above. As described above, these characteristics are maintained over a wide range of impact forces, sample types, and temperature ranges, including in some embodiments, cryogenic temperature ranges. In one configuration, the sample vessel 800 is constructed from two sheets of a flexible material. Preferably, the material retains its flexibility and structural integrity at cryogenic temperatures. As discussed above, exemplary materials include, but are not limited to, polyimide films such as Kapton™ film part number 150FN019 available from Dupont. The two sheets of material can be sealed (e.g., heat-sealed, crimped, clipped, or glued) along a border 804 on three edges. Sealing the two sheets of material on three edges creates a pouch (vessel) with one open end 806.

The open end 806 of the vessel 800 can be closed with a cap 803 directly or by way of a hub fitting 802. Both the hub fitting 802 and the cap 803 may be formed, for example, from acetyl copolymer, polypropylene, or any suitable polymer plastic. The hub fitting 802 may be slid into and secured within the opening 806 of the vessel 800 by way of any suitable mechanism, including heat bonding, crimping, clipping, heat shrinking, and/or gluing. Illustratively, a substantially gastight seal is formed between the hub fitting 802 and the inner wall of the opening 806. In certain embodiments, the inner wall near the opening 806 can be sandwiched between the hub fitting 802 and an adhesive-lined heat-shrink polyolefin tubing (e.g., Raychem TAT 125) to help affix the flexible vessel to the hub fitting 802 in a gastight manner. In other embodiments, such tubing is not necessary. The inner surface of the vessel 800 near the opening 806 (e.g., an interior surface of the vessel in opposition to the hub fitting 802) can be coated or otherwise composed of a heat-sealable material. Exemplary heat-sealable materials include, but are not limited to FEP. Such heat-sealable material can then be used to attach the flexible vessel 800 directly to the hub fitting 802. Additionally, the opening 806 can have a funnel like shape, and be employed with our without the hub fitting 802. The cap 803 is, for example, threaded to screw reversibly into the hub interface 802. In various illustrative embodiments, the cap/plug 803 may be, for example, screw-fitted, snap-fitted, pressure-fitted, or magnetically attached. Optionally, the cap may be modified by punching a ⅜ inch through port into the top, such as in the case of Fisher, p/n 14-962-26F, Pittsburg, Pa. According to other illustrative embodiments, the hub fitting 802 may be sized and shaped for reversibly sealable mating with another vessel, so that the contents of the vessel 800 may be easily transferred to the other vessel for further processing. Such a configuration is discussed in further detail below with regard to FIG. 10.

Figure 8:
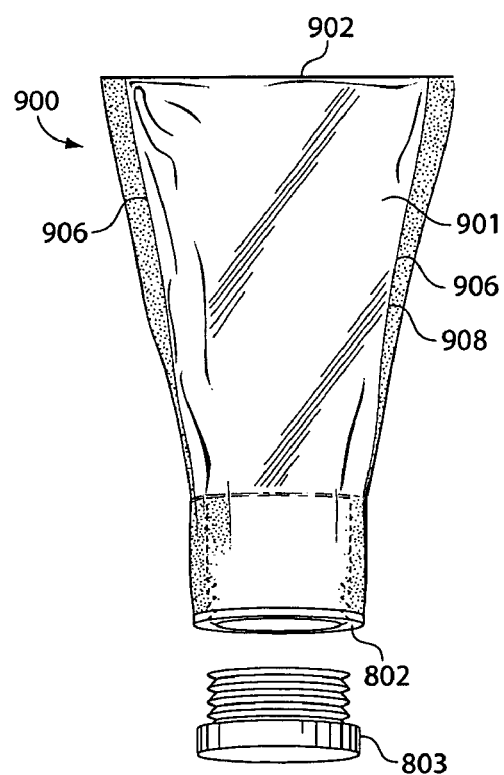
FIG. 8 depicts a sample preparation vessel according to another illustrative embodiment of the invention.

FIG. 8 depicts a sample vessel 900 according to another illustrative embodiment of the invention. As in the case of the sample vessel 800, the sample vessel 900 includes any or all of the above described nondestructive deformation characteristics. The sample vessel 900 is essentially the same as the vessel 800 except that it is formed from a single sheet of material, folded to form an enclosed bottom edge 902 and bonded along the edges 906 and 908 to form a pouch 901, as opposed to the two sheet configuration of the illustrative embodiment of FIG. 7. The vessel 900 includes the hub 802 and cap/plug 803 configuration of the vessel 800 of FIG. 8.

According to one illustrative embodiment, excluding the hub 802 and cap 803, which are preferably formed from a substantially rigid material, the entire vessel 800 and 900 is formed from a material having the above described nondestructive deformation properties.

According to various illustrative embodiments, the vessels 800 and 900 can be employed in place of the vessels 120 and 220 in any of the above described embodiments. For example, the vessels 800 and 900 can replace the vessel 120 in any of the embodiments depicted in or discussed with regard to FIG. 1, and the vessel 220 in any of the embodiments depicted in or discussed with regard to FIGS. 2A and 2B, 3A and 3B, 4, 5A-5D, and 6A-6E.

Figure 9:
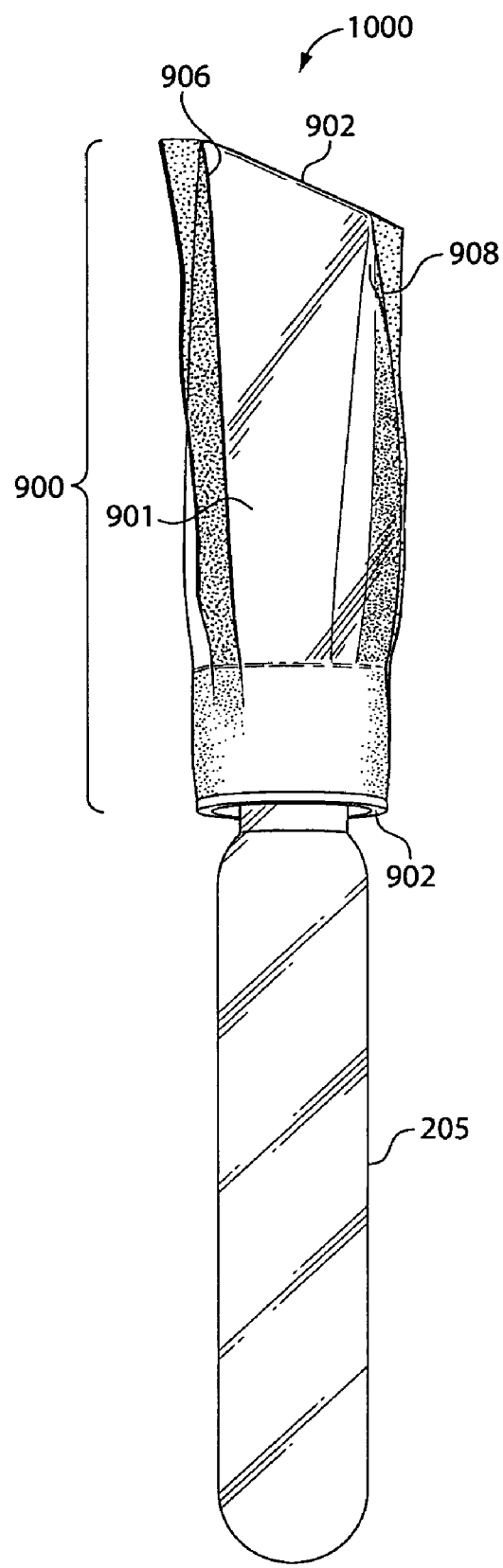
FIG. 9 depicts a sample preparation vessel attached to a processing tube, according to one illustrative embodiment of the invention.

In one example of such a replacement, FIG. 9 shows the vessel 900 of FIG. 8 interfitted with the processing vessel 205 as similarly depicted in FIGS. 2A and 2B at 203 and 243, respectively. As is the case with the configurations of FIGS. 2A and 2B, the processing vessel 205 may have an agent, reagent, buffer or other material placed in it prior to interfitting with the vessels 800 or 900. Preferably, the processing tube 205 includes a barrier for containing the material so that it does not spill into the vessels 800 or 900 at an undesirable time. According to one feature, an operator can cause the barrier to break to release the material into the sample vessel 900 or to allow the sample to be transferred to the processing vessel 205. Such transfer may be caused to occur before, after or during fragmentation. Breaking of the barrier may be caused, for example, by the fragmenting process. According to another illustrative embodiment, an operator rotates or otherwise manipulates the sample and processing vessels relative to each other to break the barrier. In another embodiment, the operator squeezes the sample vessel 900 to decrease its volume sufficiently to create a pressure against and break the barrier of the processing vessel 205.

Although FIGS. 7 and 8 are not shown in color, preferably, the pouches 801 and 901 are preferably formed from an amber, gold or yellow colored translucent material. The ornamental design of the vessels 800 and 900, generally, and the pouches 801 and 901, particularly, are considered to be part of the herein described invention. The ornamental design of the assembly 1000 is also considered to be part of the herein described invention.

Figure 10:
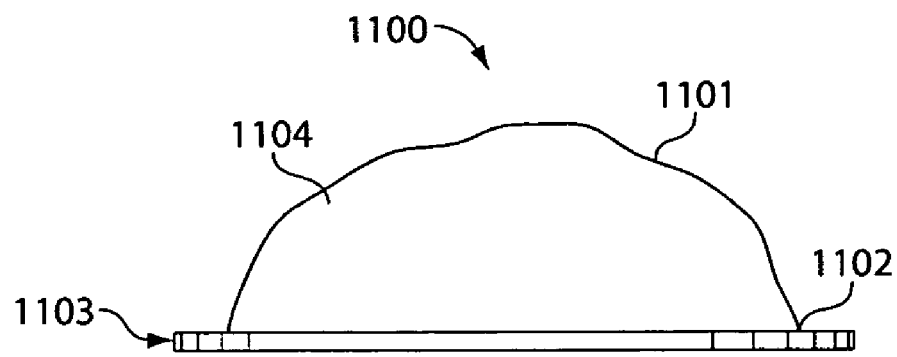
FIG. 10 depicts a sample preparation vessel formed on a substrate according to an illustrative embodiment of the invention.

FIG. 10 depicts a sample vessel 1100 according to another illustrative embodiment of the invention. The sample vessel includes a deformable wall 1101, formed as a blister pack on a substrate 1103 to form a chamber 1104. One or more layers of a flexible material of the type discussed above or other suitable material can be affixed by way of any suitable mechanism along a periphery to the surface 1102 of the substrate 1103. Although not shown, the vessel 1100 may include one or more reversibly sealable openings, for example, located on the substrate 1103 or the deformable wall 1101 for inserting and removing a sample form the chamber 1104. In operation, an impact providing device need only provide an impact to the deformable wall 1101, with the substrate 1103 braced against a stationary surface.

Figure 11:
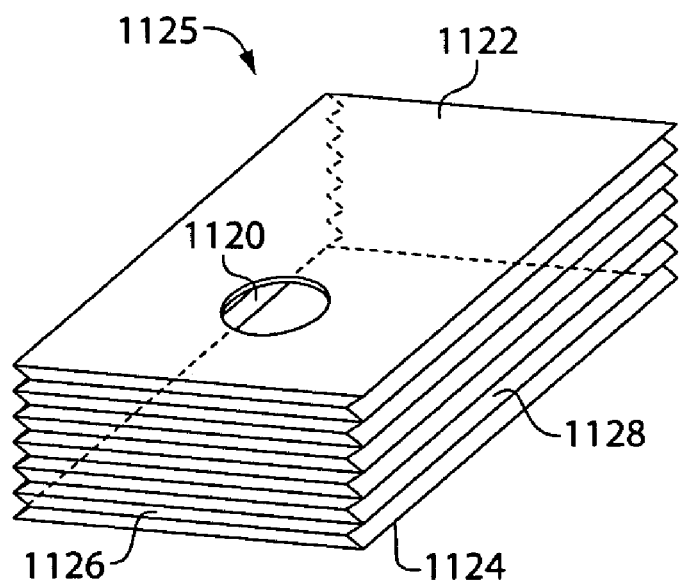
FIG. 11 depicts a sample preparation vessel having one or more accordion like sides according to another illustrative embodiment of the invention.

FIG. 11 shows a vessel 1125 according to another illustrative embodiment of the invention. As shown, the vessel 1125 includes a substantially rigid top wall 1122 and bottom wall 1124 and one or more creased accordion-like side walls 1126 and 1128. In response to an impact on either or both of the top 1122 and bottom 1124 walls, the side walls 1126 and 1128 fold and nondestructively collapse to enable a sample contained within the vessel 1125 to be fragmented between the two substantially rigid walls 1122 and 1124. The vessel 1125 also includes at least one reversibly sealable port 1120 for introducing sample into and/or removing a sample from the vessel 1125. The walls 1126 may be made from any material suitable for performing under the above described fragmentation and temperature conditions, including those materials disclosed herein. In other illustrative embodiments, the port 1120 may be located anywhere on the device vessel.

Figure 12:
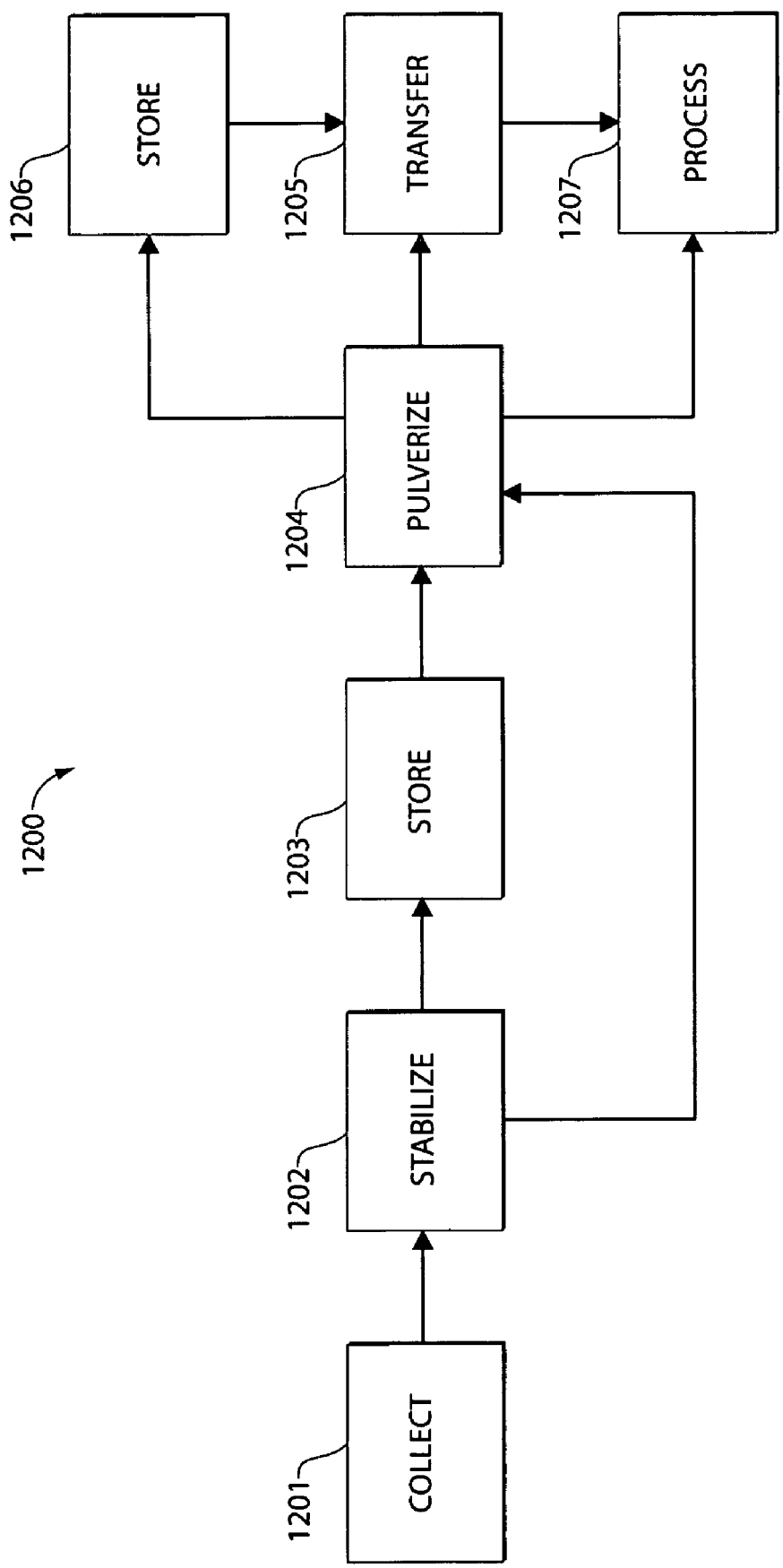
FIG. 12 is a schematic flow diagram depicting automated and/or manual methodologies by which a sample may be collected, stabilized, stored, fragmented, transferred, and/or processed according to various illustrative embodiments of the invention.

FIG. 12 depicts a flow diagram of a process 1200 for collecting, stabilizing, and fragmenting a sample according to an illustrative embodiment of the invention. The sample is initially collected at 1201. A biological or non-biological sample can be harvested and placed into a sample processing vessel, such as the vessels 120, 220, 800, 900, 1100 and 1125. The sample is inserted into the vessel via an open end or port, and the open end or port is then sealed (e.g., plugged or capped) so that the sample is contained within a closed, sample vessel. In some embodiments, the port is reversibly sealed. Given that many samples, particularly biological and non-biological samples for which an ultimate assay involves examination of a biological or chemical agent, are sensitive to contamination and/or degradation, the sample can then be stabilized at 1202. Stabilization may include, for example, thermal and/or chemical stabilization.

By way of example, stabilization 1202 may include subjecting the sample contained within the sample vessel to cryogenic temperatures. Exemplary cryogenic temperatures include temperatures less than or equal to about −20° C. (e.g., placing the sample vessel into a freezer set to −20° C., placing the sample vessel on dry ice). Further exemplary cryogenic temperatures include temperatures less than or equal to about −80° C. Other exemplary cryogenic temperatures include temperatures less than or equal to about −196° C. (e.g., placing the sample vessel into liquid nitrogen). In a preferred embodiment, the sample vessel is constructed, at least in part, from materials that nondestructively deform in a manner, such as that discussed supra, across the temperature range at which the sample is manipulated. Preferred materials include materials with rapid heat transfer characteristics (e.g., materials that rapidly transfer temperature from the external environment to the interior of the vessel such that a sample within the vessel rapidly reaches a desired temperature).

The stabilization step 1202 may also include chemical stabilization. For example, agents that inhibit degradation of sample constituents can be introduced into the vessel, or alternatively, the vessel may be treated with such constituents. These agents can be added prior to, concomitantly with, or following collection of the sample into the sample vessel. Exemplary agents include, but are not limited to, DNase inhibitors, RNase inhibitors, protease inhibitors, anti-coagulents, anti-bacterial agents, anti-fungal agents, chelating agents (e.g., EDTA, EGTA), glycerol, and/or the like.

At step 1203, following stabilization, the sample may be stored for some period of time prior to pulverization. Prior to storage, the sample vessel containing the sample may be marked with a label or bar code to facilitate later identification. The sample can be shipped and stored at a separate location or can be stored at the site of sample collection. Depending on the particular sample, storage illustratively occurs at cryogenic temperatures ranging from about −20° C. to about −196° C. However, the invention contemplates that for certain samples and certain applications, storage can occur at temperatures greater than −20° C., for example, storage can occur at room temperature.

Following stabilization at 1202, rather than be stored at 1203, the sample may be pulverized/fragmented at 1204. As described above, the fragmenting step 1204 may include contacting a sample vessel containing a sample with a mechanical force, sufficient to achieve the desired fragmentation. According to the various illustrative embodiments, the sample vessel includes at least a portion that is nondestructively deformable to enable the mechanical force to be transferred to the sample through the vessel while maintaining the sample in isolation from the external environment, generally, and the impact surface or surfaces, particularly. The invention thus provides non-contact, mechanical fragmentation of the sample contained in the sample vessel.

As described supra, the mechanical impact force to the sample may be provided by suitable mechanism, including for example, a hammer. However, in a preferred embodiment, a mechanical impact providing device, such as that described with regard to FIGS. 4 and 5.

As depicted in FIG. 12, the fragmentation step 1204 (as described in the previous two paragraphs) may occur following some period of storage. Note that this period of storage can vary based on the particular sample, its intended use, etc. Exemplary storage periods include short term storage for minutes (e.g., less than or equal to 30 minutes) or hours (e.g., less than or equal to 1, 2, 5, 10, or 12 hours). Further exemplary storage periods include overnight storage or storage for about 1-3 days, 3-5 days, 1 week, 2 weeks, 4 weeks, or greater than 4 weeks. Still further exemplary storage periods include long range storage for 3-6 months, 6-12 months, 1-2 years, greater than 2 years, 2-10 years, or longer.

Following fragmentation in step 1204, the sample vessel may be further marked, for example, to provide information relevant fragmentation, such as the degree to which the sample has been fragmented. Next, the sample may be stored in step 1206 in a similar fashion to that described above with respect to step 1206, transferred in step 1205 for further processing in step 1207, or further processed in step 1207 without transferring the sample out of the original sample vessel.

Transferring to a processing vessel at 1205 can occur by directly attaching the processing vessel to the sample vessel, inverting the sample vessel, and optionally flicking or tapping the sample vessel so that substantially all of the sample is transferred from the sample vessel into the processing vessel. Alternatively, sample transfer 1205 can occur without directly attaching the processing vessel to the sample vessel. Transfer 1205 may occur at cryogenic temperatures in the ranges discussed above, for example, by pre-chilling the processing vessel prior to sample transfer.

In certain embodiments, the sample transfer 1205 is facilitated by addition of a liquid to either the sample vessel or the processing vessel. The liquid may include a buffer or solvent and may optionally include agents that prevent degradation of sample, such as DNase inhibitors, RNase inhibitors, protease inhibitors, anti-coagulents, anti-bacterial agents, anti-fungal agents, chelating agents (e.g., EDTA, EGTA), glycerol and/or the like. Such agents may be particularly useful if the sample thaws during sample transfer or if further processing of the sample is not to occur at cryogenic temperatures. When a liquid is used to facilitate sample transfer 1205, the liquid can be added to the sample vessel prior to transfer of any material to the processing vessel. Alternatively, the liquid can be added to the sample vessel after the sample is transferred to the processing vessel to ensure that substantially all of the sample is transferred to the processing vessel. As indicated in FIG. 12, the sample transfer step 1205 may also occur after a period of storage at step 1206.

Further processing at 1207 may include, without limitation, cooling; heating; fluidizing, mixing, stirring, disrupting, increasing permeability of a component of, enhancing a reaction of, sterilizing, and/or further fragmenting the sample. Such further processing is described in co-pending, co-owned U.S. patent application Ser. No. 10,777,014, entitled Apparatus and Methods for Controlling Sonic Treatment," the entire disclosure of which is incorporated above by reference. Further processing may also include, any detection, measurement, identification or other analysis performed on the sample.

Figure 13:
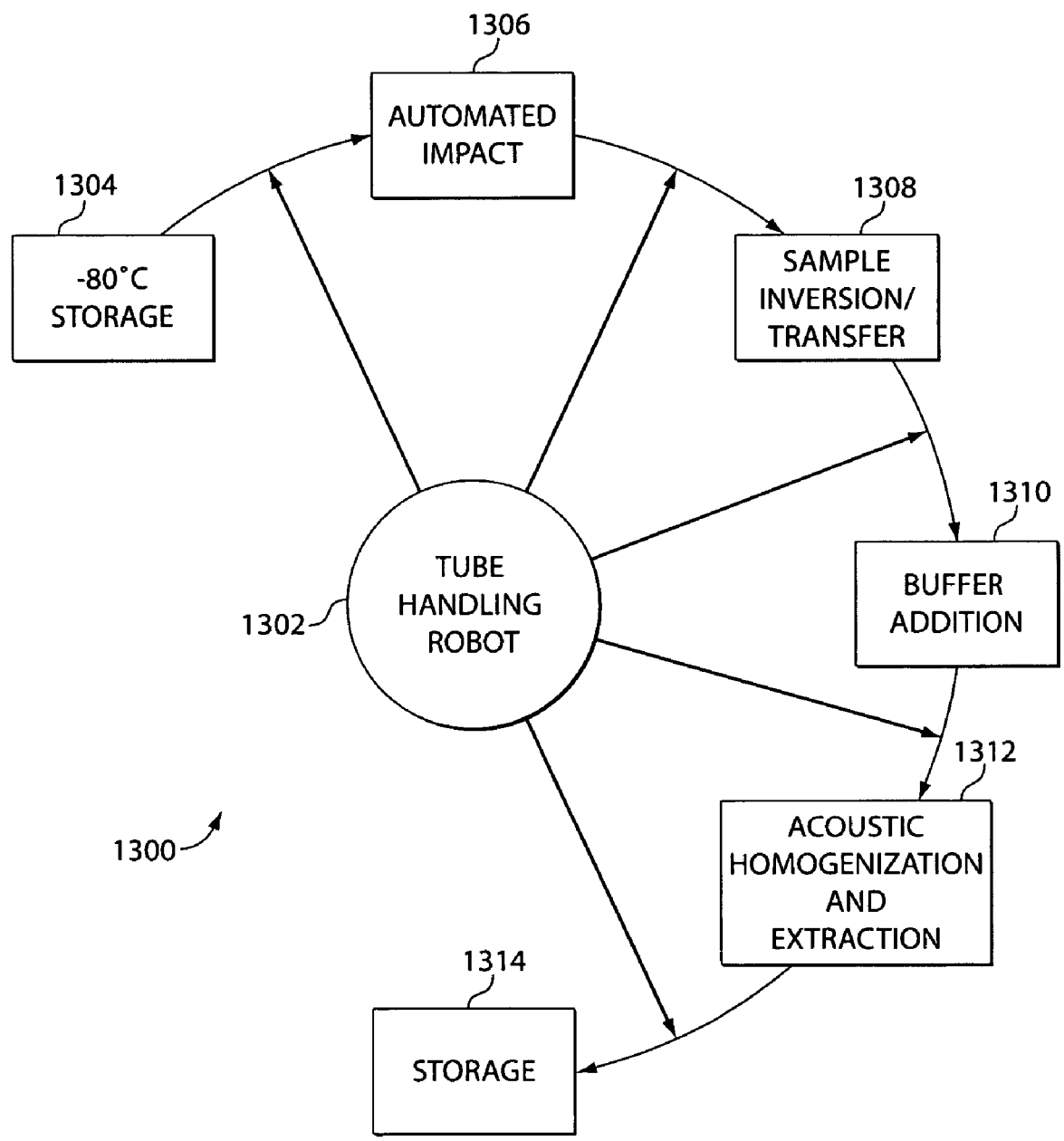
FIG. 13 is a conceptual diagram depicting the invention being employed in a robot-assisted sample preparation/treatment system according to an illustrative embodiment of the invention.

According to an additional illustrative embodiment, the invention is directed to systems and methods for processing a sample employing an automated vessel handling robot. Such a robot may perform any or all of the vessel handling steps of FIG. 12. FIG. 13 shows another diagram 1300 illustrative of an approach using an vessel handling robot 1302. As shown in FIG. 13, the vessel handling robot 1302 may be employed for retrieving a sample vessel of the type described herein from a storage location 1304, providing it to an impact providing device 1306 for fragmenting the sample, inverting the sample vessel to transfer the fragmented sample into a second vessel at 1308, adding an appropriate agent, reagent, buffer or other material, as desired, to the second vessel at 1310, providing the vessel to a device for treating the sample with focused acoustic energy, for example, for homogenization and/or extraction at step 1312, and placing the homogenized sample in a storage location at 1314. The storage location from which the sample vessel is retrieved at 1304 and the storage location to which the homogenized sample is placed at 1314 may or may not be the same storage location. Additionally, storage may or may occur at any suitable temperature including cryogenic and non-cryogenic temperatures. Ultrasonic processes of the type employed on the second vessel are described in U.S. patent application Ser. No. 10,777,014, the entire content of which is incorporated above by reference. According to a variation of this aspect of the invention, the sample is not transferred to a second vessel at 1302. Instead, the sample vessel is used for the entire process, and transferred directly from 1306 to 1310. Additionally, in some illustrative embodiments, the acoustic treatment of 1312 may be skipped.

According to a further feature, the throughput of the above described automated process may be increased by having multiple samples processed in a batch mode. For example, 96 samples may be fragmented either serially or in parallel. The samples may be transferred from process to process and even from sample vessels to further processing vessls in batch mode. Additionally, the sample vessels may include dimples or indents on an interior surface to localize the sample. Samples may vary in size, and in one example are about 5 mg. As discussed above, the samples may be maintained at or above cryogenic temperatures, depending on the sample.

The methods and systems of the invention are useful in any of a number of applications in which a sample is to be fragmented to smaller pieces of the specimen prior to further analysis of the sample in whole or in part. The methods, systems and devices of the invention allow non-direct contact fragmentation of a sample and furthermore allow fragmentation under conditions that prevent degradation of constituents of the sample. The invention can be used to collect and process a range of biological and non-biological samples. Accordingly, the invention has a wide array of applications, for example, in the fields of medical research, medical diagnostics, agricultural research, food safety, bio- and chemical hazard management and safety, and the like.

By way of example, many assays, including diagnostic assays, are based on the detection of nucleic acids or proteins contained within a sample. Such assays include, but are not limited to, PCR, RT-PCR, hybridization to nucleic acid or protein-based micro-arrays, and immunohistochemistry. Reproducible analysis using these assays requires "clean" starting samples (e.g., samples that have not been contaminated or exposed to degradation agents) that have been processed to allow access to their constituent elements (e.g., samples that have been sufficiently fragmented and homogenized to allow access to nucleic acids, proteins, and small molecule constituents contained within the sample).

By way of a more particular example of the medical application of the invention, it may be used to process pathological and/or non-pathological tissue samples harvested from a patient. Such samples include, but are not limited to, putative tumor samples taking during a biopsy. Prior to analysis of the nucleic acid, protein, or small molecule constituents of the tissue sample, the sample can be collected, stabilized, and pulverized using the above described methods, systems and devices of the invention.

By way of a further non-medical example, the invention can be used in the food industry. One issue encountered in the food industry is that of possible bacterial, viral, fungal, prion and/or chemical contamination. Presence of such possible contaminants within a sample of a food product and/or ingredient may be assayed using available biochemical and/or molecular biological tests. Prior to biochemical and/or molecular analysis, a given sample of food may be collected, stabilized to prevent degradation of the bacterial and/or chemical agents that one wishes to detect, and pulverized to yield smaller specimens amenable to further processing and analysis, according to the above described illustrative embodiments of the invention.

By way of another example, the methods, systems and devices of the invention may be used in industries such as the petro-chemical industry. Analysis of the mineral composition of particular solid samples at the molecular, chemical, and/or atomic level are useful in this industry for identifying, for example, commercially advantageous lodes, outcroppings, and/or drilling sites. Solid samples such as rocks and mineral deposits are often too large to be directly analyzed using molecular and/or chemical tools. Accordingly, such samples can be collected, stabilized, and fragment to yield smaller specimens amenable to further processing and analysis, according to the above described illustrative embodiment of the invention.

The invention now being generally described, it will be more readily understood by reference to the following examples which are included merely for purposes of illustration of certain aspects and embodiments of the invention, and are not intended to limit the scope of invention.

EXAMPLE A

Referring to FIGS. 14A-14D, brewers yeast was aliquoted into a vessel formed from a 2 mil Kapton™ film part number 150FN019, available from Dupont, similar to those depicted in FIGS. 7, 8, and 9, however, without a rigid hub and/or cap. As shown in FIG. 14A, dry yeast spores were inserted into the vessel, the mass of the spores was 35 mg. As shown in FIG. 14B, the open top of the vessel was folded over and held in place with a large paper clip. The air space in the pouch was minimized. The spores were located at the bottom of the vessel. As shown in FIG. 14C, depending on size, the spores may be located differently in the vessel. The vessel was then inserted into a manual, vertical hammer/anvil device. The hammer was raised released three times. As shown in FIG. 14D, the resultant yeast spores were visibly cracked and opened. As also shown in FIG. 14D, the vessel was opened and the fragmented spores were transferred to a test tube. A PBS salt solution was then added. The resultant yeast particles were and PBS salt solution was then subjected to a focused acoustic extraction, such as that disclosed in U.S. patent application Ser. No. 10,777,014, the entire content of which is incorporated above by reference. The supernatant was visibly cloudy after the ultrasonic extraction, indicating lysis and extraction of biomolecules. In contrast, exposing a control to the same acoustic extraction process, without first fragmenting/pre-cracking the spores, resulted in an essentially clear solution, indicating no lysis or biomolecule extraction. One advantage of the fragmentation process of the invention is that it avoids the using any enzymes or detergents. The process of the invention is also rapid and may be run at cryogenic temperatures.

EXAMPLE B

Referring generally to the device shown FIGS. 1 and 8, a sample vessel was made by heat-sealing a 2 mil Kapton™ film part number 150FN019 available from Dupont on three sides. The dimension of the two sealed sides was about 2.5 inches and the width was about 1.5 inch. A tissue sample of 1 gram of fresh beefsteak was placed into the vessel. The open end of the vessel was clamped and the vessel with the tissue was placed into a −80° C. freezer for 30 minutes. The vessel with the sample now frozen was removed and placed on a previously chilled metal plate. Another metal plate was placed over the tissue area of the vessel. A urethane 5-pound hammer was struck once to pulverize the chilled tissue sample into smaller pieces. The vessel retained flexibility and did not tear. The pulverized pieces were transferred to a borosilicate 16 mm×100 mm culture tube for further processing and 2 ml of distilled water was added. The culture tube with the pulverized tissue and distilled water was homogenized using Covaris E200 system (Woburn, Mass.) for 30 seconds. The Covaris E200 is described in relevant part in U.S. patent application Ser. No. 10,777,014 incorporated above by reference.

EXAMPLE C

Referring generally to FIGS. 2 and 9, a sample vessel was constructed from a modified polypropylene screw cap that fits a 16 mm×100 mm culture tube. A $\frac{3}{8}^{th}$ inch opening was punched through the top. A pouch formed from Kapton™ (part number 150FN019 available from) film was affixed to the polypropylene screw cap with ½ inch of heat-shrink tubing. A sample of previously-frozen liver was inserted through the opening in the screw cap into the pouch and the cap was sealed. The loaded vessel and sample were placed on dry ice. The vessel was laid on a metal plate previously chilled to −80° C. and a block of Delrin (1 inch×1 inch×3 inch) was placed over the tissue area of the vessel. A metal hammer was used to impact the block thereby transferring the impact through the flexible Kapton™ film and to the brittle liver sample. The vessel containing the fragmented sample was screw attached to a previously chilled borosilicate tube in an end-to-end fashion. The sample vessel was then inverted to transfer the contents to the borosilicate tube. The sample vessel was removed and 2 ml of GITC-based RNA stabilization buffer was added to the borosilicate tube. The sample contained within the borosilicate tube was loaded into Covaris E200 system and thoroughly homogenized within 15 seconds.

Those skilled in the art will know or be able to ascertain using no more than routine experimentation, many equivalents to the embodiments and practices described herein. Accordingly, it will be understood that the invention is not to be limited to the illustrative embodiments disclosed herein, but is to be understood from the following claims. It should be noted that any operable combinations between any of the systems, methods, and devices described herein are considered to be patentable subject matter, including any such operable combinations involving the disclosure of U.S. patent application Ser. No. 10,777,014, the disclosure of which is above incorporated by reference.

What is claimed is:

1. A vessel for containing a sample, the vessel, comprising a reversibly sealable chamber for containing the sample, a flexible portion of the reversibly sealable chamber, the flexible portion of the chamber being flexible enough to allow the vessel to deform nondestructively in response to a mechanical impact sufficient to fragment the sample into a plurality of sample fragments, a reversibly sealable port, which in combination with the reversibly sealable chamber, forms a barrier between the sample and an external environment, and a security feature for interacting with a corresponding security feature on a device for providing the mechanical impact.

2. The vessel of claim 1 wherein the flexible portion is formed from a material that remains nondestructively deformable at temperatures less than about −40° C.

3. The vessel of claim 1, wherein the flexible portion is formed from a material that remains nondestructively deformable at temperatures less than about −50° C.

4. The vessel of claim 1, wherein the flexible portion is formed from a material that remains nondestructively deformable at temperatures less than about −60° C.

5. The Vessel of claim 1, wherein the flexible portion is formed from a material that remains nondestructively deformable at temperatures less than about −70° C.

6. The vessel of claim 1, wherein the flexible portion is formed from a material that remains nondestructively deformable at temperatures between about −80° C. and about −196° C.

7. The vessel of claim 1, wherein the flexible portion is formed from a material that does not crack, tear, or rip when exposed to the mechanical impact.

8. The vessel of claim 1, wherein the flexible portion is formed from a material that deforms nondestructively in response to the mechanical impact providing an impact energy transfer of at least about 10 Joules.

9. The vessel of claim 1, wherein the flexible portion is formed from a material that deforms nondestructively in response to the mechanical impact providing an impact energy transfer of at least about 10 Joulcs.

10. The vessel of claim 1, wherein the flexible portion is formed from a material that deforms nondestructively in response to the mechanical impact providing an impact energy transfer of at least about 12, Joules.

11. The vessel of claim 1, wherein the flexible portion is formed from a material that deforms nondestructively in response to the mechanical impact providing an impact energy transfer of at least about 14 Joules.

12. The vessel of claim 1, wherein at least a portion of the vessel that is contacted by the mechanical impact has a thickness of between about 0.5 and about 5 mil.

13. The vessel of claim 1, wherein at least a portion of the vessel that is contacted by the mechanical impact has a thickness of less than about 1 mil.

14. The vessel of claim 1, wherein at least a portion of the vessel that is contacted by the mechanical impact has a thickness of less than about 2 mil.

15. The vessel of claim 1, wherein at least a portion of the vessel that is contacted by the mechanical impact has a thickness of less than about 3 mil.

16. The vessel of claim 1, wherein at least a portion of the vessel that is contacted by the mechanical impact has a thickness of less than about 4 mil.

17. The vessel of claim 1, wherein at least a portion of the vessel that is contacted by the mechanical impact has a thickness of less than about 5 mil.

18. The vessel of claim 1, wherein at least a portion of the vessel that is contacted by the mechanical impact has a thickness of less than about 3.5 mil.

19. The vessel of claim 1, wherein at least a portion of the vessel that is contacted by the mechanical impact has a thickness of less than about 4.0 mil.

20. The vessel of claim 1, wherein at least a portion of the vessel that is contacted by the mechanical impact has a thickness of less than about 5.0 mil.

21. The vessel of claim 1 including a second reversibly sealable port for removing the sample from the chamber.

22. The vessel of claim 1, wherein at least the flexible portion is formed at least in part from polymide.

23. The vessel of claim 1, wherein at least the flexible portion is formed at least in part from polysulfone.

24. The vessel of claim 1, wherein at least the flexible portion is formed at least in part from fluorinated polymer.

25. The vessel of claim 1, wherein at least the flexible portion is formed at least in part from Kapton™ film.

26. The vessel of claim 1, wherein at least the flexible portion is formed at least in part from a liquid crystal polymer.

27. The vessel of claim 1, wherein the structural barrier is formed from two pieces of a film material bonded together along their peripheries and reversibly sealed.

28. The vessel of claim 1, wherein the structural barrier is formed from a single piece of a film material folded and bonded together along a portion of its periphery and reversibly sealed in a substantially air tight fashion.

29. The vessel of claim 1, wherein the reversibly sealable port is sized and shaped for sealably mating with a second vessel.

30. The vessel of claim 1, wherein an internal surface of the structural barrier is treated with at least one of DNase inhibitors, RNase inhibitors, protease inhibitors, anti-coagulants, anti-bacterial agents, anti-fungal agents, chelating agents, and glycerol.

31. A vessel for containing a sample, the vessel comprising
a reversibly salable chamber for containing the sample,
a flexible portion of the reversibly sealable chamber, the flexible portion of the chamber being flexible enough to allow the vessel to deform nondestructively in response to a mechanical impact sufficient to fragment the sample into a plurality of sample fragments at temperatures below about −40° C.

32. A vessel for containing a sample, the vessel comprising
a reversibly sealable chamber for containing the sample,
a flexible portion of the reversibly sealable chamber, the flexible portion of the chamber being flexible enough to allow the vessel to deform nondestructively in response to a mechanical impact sufficient to fragment the sample into a plurality of sample fragments at temperatures below about −40° C., wherein the sample includes at least one of a seed, bone, rock, stone, sand, glass, metal, tree bark, and fragments and combinations thereof.

33. A method for processing a sample, comprising
employing a vessel forming a reversibly sealable barrier between a sample contained within the vessel and an external environment, the vessel including a flexible portion flexible enough to allow the vessel to deform nondestructively in response to a mechanical impact sufficient to fragment the sample in the vessel into a plurality of sample fragments,
exposing the vessel to the mechanical impact, and
mating the vessel with a second vessel to provide a fluid interconnection between the vessel and the second vessel, and transferring the plurality of sample fragments from the vessel to the second vessel.

34. The method of claim 33 including exposing the vessel to the mechanical impact with the sample at a temperature below about −50° C.

35. The method of claim 33 including exposing the vessel to the mechanical impact with the sample at a temperature below about −60° C.

36. The method of claim 33 including exposing the vessel to the mechanical impact with the sample at a temperature below about −70° C.

37. The method of claim 33 including exposing the vessel to the mechanical impact at with the sample at a temperature below about −80° C.

38. The method of claim 33, wherein the mechanical impact provides an impact energy transfer of at least about 10 Joules.

39. The method of claim 33, wherein the mechanical impact provides an impact energy transfer of at least about 12 Joules.

40. The method of claim 33, wherein the mechanical impact provides an impact energy transfer of at least about 14 Joules.

41. The method of claim 33 including treating the sample with focused acoustic energy subsequent to exposing the vessel to the mechanical impact.

42. The method of claim 41 including storing the sample subsequent to treating the sample with the focused acoustic energy.

43. The method of claim 42 including analyzing parameters of the sample subsequent treating the sample with the focused acoustic energy.

44. The method of claim 43 including employing an automated robot to perform one or more transfers of the sample between suitable devices for exposing the sample to the mechanical impact, treating the sample with focused acoustic energy, and analyzing the sample subsequent to treating the sample with the focused acoustic energy.

* * * * *

UNITED STATES PATENT AND TRADEMARK OFFICE
CERTIFICATE OF CORRECTION

PATENT NO. : 7,328,628 B2  Page 1 of 1
APPLICATION NO. : 11/001988
DATED : February 12, 2008
INVENTOR(S) : Laugharn, Jr. et al.

It is certified that error appears in the above-identified patent and that said Letters Patent is hereby corrected as shown below:

Claim 5, col. 24, line 42, change "Vessel" to --vessel--; and

Claim 31, col. 25, line 58, change "salable" to --sealable--.

Signed and Sealed this

First Day of July, 2008

JON W. DUDAS
*Director of the United States Patent and Trademark Office*